(12) United States Patent
Guerra

(10) Patent No.: US 8,197,633 B2
(45) Date of Patent: *Jun. 12, 2012

(54) METHOD FOR MANUFACTURING AN END EFFECTOR ASSEMBLY

(75) Inventor: Paul Guerra, Los Gatos, CA (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,679

(22) Filed: Mar. 15, 2011

(65) Prior Publication Data

US 2011/0162796 A1    Jul. 7, 2011

Related U.S. Application Data

(62) Division of application No. 11/529,414, filed on Sep. 28, 2006, now Pat. No. 7,922,953.

(60) Provisional application No. 60/722,186, filed on Sep. 30, 2005.

(51) Int. Cl.
    *C09J 5/00* (2006.01)
(52) U.S. Cl. ....................................... 156/314
(58) Field of Classification Search ................... 156/314
    See application file for complete search history.

(56) References Cited

U.S. PATENT DOCUMENTS

| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,176,479 A | 10/1939 | Willis |
| 2,305,156 A | 4/1941 | Grubel |

(Continued)

FOREIGN PATENT DOCUMENTS

CA    2 104 423    2/1994

(Continued)

OTHER PUBLICATIONS

U.S. Appl. No. 08/926,869, filed Sep. 10, 1997, James G. Chandler.

(Continued)

*Primary Examiner* — Katarzyna Wryozebski Lee
*Assistant Examiner* — Daniel Lee

(57) ABSTRACT

A method of manufacturing a jaw member of an end effector assembly for use with an electrosurgical instrument is disclosed that includes the steps of providing an electrically conductive tissue engaging plate and a jaw support; covering one side of the electrically conductive tissue engaging plate with an electrically insulative, thermally non-degrading coating; placing and securing the electrically conductive tissue engaging plate and the jaw support into a jaw mold; and introducing a liquid substance into the jaw mold and allowing the liquid substance to cure around the electrically conductive tissue engaging plate and the jaw support. Alternatively, the method includes the steps of: providing an electrically conductive tissue engaging plate and a jaw support; covering one side of the electrically conductive tissue engaging plate with an electrically insulative, thermally non-degrading coating; and securing the side of the electrically conductive tissue engaging plate onto the jaw support with an adhesive.

5 Claims, 8 Drawing Sheets

U.S. PATENT DOCUMENTS

| | | | |
|---|---|---|---|
| 2,245,030 A | 6/1941 | Gottesfeld et al. |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | De Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | DiGeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 371,664 A | 10/1987 | Brannan et al. |
| 4,725,395 A | 2/1988 | Gasparaitis et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,973,801 A | 11/1990 | Frick et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,056 A | 10/1993 | Hasson |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |

| Patent | Date | Inventor |
|---|---|---|
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,290,287 A | 3/1994 | Boebel et al. |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,900 A | 3/1995 | Slater et al. |
| 5,397,325 A | 3/1995 | Della Badia et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,479 A | 8/1995 | Bressi, Jr. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,809 A | 10/1995 | Janssen |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |
| 5,484,436 A | 1/1996 | Eggers et al. |
| 5,493,899 A | 2/1996 | Beck et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |

| | | | | | |
|---|---|---|---|---|---|
| 5,630,833 A | 5/1997 | Katsaros et al. | 5,820,630 A | 10/1998 | Lind |
| 5,637,110 A | 6/1997 | Pennybacker et al. | 5,824,978 A | 10/1998 | Karasik et al. |
| 5,638,003 A | 6/1997 | Hall | 5,827,271 A | 10/1998 | Buysse et al. |
| 5,639,403 A | 6/1997 | Ida et al. | 5,827,274 A | 10/1998 | Bonnet et al. |
| 5,643,294 A | 7/1997 | Tovey et al. | 5,827,279 A | 10/1998 | Hughett et al. |
| 5,647,869 A | 7/1997 | Goble et al. | 5,827,281 A | 10/1998 | Levin |
| 5,647,871 A | 7/1997 | Levine et al. | 5,827,323 A | 10/1998 | Klieman et al. |
| 5,649,959 A | 7/1997 | Hannam et al. | 5,827,548 A | 10/1998 | Lavallee et al. |
| 5,655,650 A | 8/1997 | Naitou | 5,830,212 A | 11/1998 | Cartmell et al. |
| 5,658,281 A | 8/1997 | Heard | 5,833,690 A | 11/1998 | Yates et al. |
| D384,413 S | 9/1997 | Zlock et al. | 5,833,695 A | 11/1998 | Yoon |
| 5,662,667 A | 9/1997 | Knodel | 5,836,072 A | 11/1998 | Sullivan et al. |
| 5,665,100 A | 9/1997 | Yoon | D402,028 S | 12/1998 | Grimm et al. |
| 5,667,526 A | 9/1997 | Levin | 5,843,080 A | 12/1998 | Fleenor et al. |
| 5,674,220 A | 10/1997 | Fox et al. | 5,849,022 A | 12/1998 | Sakashita et al. |
| 5,674,229 A | 10/1997 | Tovey et al. | 5,851,214 A | 12/1998 | Larsen et al. |
| 5,681,282 A | 10/1997 | Eggers et al. | 5,853,412 A | 12/1998 | Mayenberger |
| 5,688,270 A | 11/1997 | Yates et al. | 5,859,527 A | 1/1999 | Cook |
| 5,690,652 A | 11/1997 | Wurster et al. | 5,860,976 A | 1/1999 | Billings et al. |
| 5,690,653 A | 11/1997 | Richardson et al. | 5,865,361 A | 2/1999 | Milliman et al. |
| 5,693,051 A | 12/1997 | Schulze et al. | 5,876,401 A | 3/1999 | Schulze et al. |
| 5,693,920 A | 12/1997 | Maeda | 5,876,410 A | 3/1999 | Petillo |
| 5,695,522 A | 12/1997 | LeMaire, III et al. | 5,876,412 A | 3/1999 | Piraka |
| 5,700,261 A | 12/1997 | Brinkerhoff | 5,882,567 A | 3/1999 | Cavallaro et al. |
| 5,700,270 A | 12/1997 | Peyser et al. | D408,018 S | 4/1999 | McNaughton |
| 5,702,390 A | 12/1997 | Austin et al. | 5,891,141 A | 4/1999 | Rydell |
| 5,707,369 A | 1/1998 | Vaitekunas et al. | 5,891,142 A | 4/1999 | Eggers et al. |
| 5,709,680 A | 1/1998 | Yates et al. | 5,893,863 A | 4/1999 | Yoon |
| 5,713,895 A | 2/1998 | Lontine et al. | 5,893,875 A | 4/1999 | O'Connor et al. |
| 5,716,366 A | 2/1998 | Yates | 5,893,877 A | 4/1999 | Gampp, Jr. et al. |
| 5,720,742 A | 2/1998 | Zacharias | 5,897,563 A | 4/1999 | Yoon et al. |
| 5,720,744 A | 2/1998 | Eggleston et al. | 5,902,301 A | 5/1999 | Olig |
| 5,722,421 A | 3/1998 | Francese et al. | 5,906,630 A | 5/1999 | Anderhub et al. |
| 5,725,536 A | 3/1998 | Oberlin et al. | 5,908,420 A | 6/1999 | Parins et al. |
| 5,727,428 A | 3/1998 | LeMaire, III et al. | 5,908,432 A | 6/1999 | Pan |
| 5,735,848 A | 4/1998 | Yates et al. | 5,911,719 A | 6/1999 | Eggers |
| 5,743,906 A | 4/1998 | Parins et al. | 5,913,874 A | 6/1999 | Berns et al. |
| 5,752,973 A | 5/1998 | Kieturakis | 5,921,916 A | 7/1999 | Aeikens et al. |
| 5,755,717 A | 5/1998 | Yates et al. | 5,921,984 A | 7/1999 | Sutcu et al. |
| 5,759,188 A | 6/1998 | Yoon | 5,925,043 A | 7/1999 | Kumar et al. |
| 5,762,255 A | 6/1998 | Chrisman et al. | 5,928,136 A | 7/1999 | Barry |
| 5,762,609 A | 6/1998 | Benaron et al. | 5,935,126 A | 8/1999 | Riza |
| 5,766,130 A | 6/1998 | Selmonosky | 5,938,589 A | 8/1999 | Wako et al. |
| 5,766,166 A | 6/1998 | Hooven | 5,941,869 A | 8/1999 | Patterson et al. |
| 5,766,170 A | 6/1998 | Eggers | 5,944,718 A | 8/1999 | Dafforn et al. |
| 5,766,196 A | 6/1998 | Griffiths | 5,951,545 A | 9/1999 | Schilling et al. |
| 5,769,849 A | 6/1998 | Eggers | 5,951,546 A | 9/1999 | Lorentzen |
| 5,772,655 A | 6/1998 | Bauer et al. | 5,951,549 A | 9/1999 | Richardson et al. |
| 5,772,670 A | 6/1998 | Brosa | 5,954,720 A | 9/1999 | Wilson et al. |
| 5,776,128 A | 7/1998 | Eggers | 5,954,731 A | 9/1999 | Yoon |
| 5,776,130 A | 7/1998 | Buysse et al. | 5,954,733 A | 9/1999 | Yoon |
| 5,776,156 A | 7/1998 | Shikhman | 5,957,923 A | 9/1999 | Hahnen et al. |
| 5,779,646 A | 7/1998 | Koblish et al. | 5,957,937 A | 9/1999 | Yoon |
| 5,779,701 A | 7/1998 | McBrayer et al. | 5,960,544 A | 10/1999 | Beyers |
| 5,779,727 A | 7/1998 | Orejola | 5,961,514 A | 10/1999 | Long et al. |
| 5,781,048 A | 7/1998 | Nakao et al. | 5,964,758 A | 10/1999 | Dresden |
| H1745 H | 8/1998 | Paraschac | D416,089 S | 11/1999 | Barton et al. |
| 5,791,231 A | 8/1998 | Cohn et al. | 5,976,132 A | 11/1999 | Morris |
| 5,792,137 A | 8/1998 | Carr et al. | 5,984,932 A | 11/1999 | Yoon |
| 5,792,165 A | 8/1998 | Klieman et al. | 5,984,938 A | 11/1999 | Yoon |
| 5,792,177 A | 8/1998 | Kaseda | 5,984,939 A | 11/1999 | Yoon |
| 5,797,537 A | 8/1998 | Oberlin et al. | 5,989,277 A | 11/1999 | LeMaire, III et al. |
| 5,797,927 A | 8/1998 | Yoon | 5,993,466 A | 11/1999 | Yoon |
| 5,797,938 A | 8/1998 | Paraschac et al. | 5,993,467 A | 11/1999 | Yoon |
| 5,797,941 A | 8/1998 | Schulze et al. | 5,993,474 A | 11/1999 | Ouchi |
| 5,797,958 A | 8/1998 | Yoon | 5,997,565 A | 12/1999 | Inoue |
| 5,797,959 A | 8/1998 | Castro et al. | 6,004,332 A | 12/1999 | Yoon et al. |
| 5,800,448 A | 9/1998 | Banko | 6,004,335 A | 12/1999 | Vaitekunas et al. |
| 5,800,449 A | 9/1998 | Wales | 6,010,516 A | 1/2000 | Hulka et al. |
| 5,807,393 A | 9/1998 | Williamson, IV et al. | 6,010,519 A | 1/2000 | Mawhirt et al. |
| 5,810,764 A | 9/1998 | Eggers et al. | 6,017,354 A | 1/2000 | Culp et al. |
| 5,810,805 A | 9/1998 | Sutcu et al. | 6,017,358 A | 1/2000 | Yoon et al. |
| 5,810,808 A | 9/1998 | Eggers | 6,021,693 A | 2/2000 | Feng-Sing |
| 5,810,811 A | 9/1998 | Yates et al. | 6,024,741 A | 2/2000 | Williamson et al. |
| 5,810,877 A | 9/1998 | Roth et al. | 6,024,743 A | 2/2000 | Edwards |
| 5,814,043 A | 9/1998 | Shapeton | 6,024,744 A | 2/2000 | Kese et al. |
| 5,814,054 A | 9/1998 | Kortenbach et al. | 6,027,522 A | 2/2000 | Palmer |
| 5,817,083 A | 10/1998 | Shemesh et al. | 6,030,384 A | 2/2000 | Nezhat |
| 5,817,119 A | 10/1998 | Klieman et al. | 6,033,399 A | 3/2000 | Gines |

| | | | | | | |
|---|---|---|---|---|---|---|
| 6,039,733 | A | 3/2000 | Buysse et al. | 6,309,404 | B1 | 10/2001 | Krzyzanowski |
| 6,041,679 | A | 3/2000 | Slater et al. | 6,319,262 | B1 | 11/2001 | Bates et al. |
| 6,050,995 | A | 4/2000 | Durgin | 6,319,451 | B1 | 11/2001 | Brune |
| 6,050,996 | A | 4/2000 | Schmaltz et al. | 6,322,561 | B1 | 11/2001 | Eggers et al. |
| 6,053,914 | A | 4/2000 | Eggers et al. | 6,322,580 | B1 | 11/2001 | Kanner |
| 6,053,933 | A | 4/2000 | Balazs et al. | 6,325,795 | B1 | 12/2001 | Lindemann et al. |
| D424,694 | S | 5/2000 | Tetzlaff et al. | 6,329,778 | B1 | 12/2001 | Culp et al. |
| D425,201 | S | 5/2000 | Tetzlaff et al. | 6,334,860 | B1 | 1/2002 | Dorn |
| 6,059,782 | A | 5/2000 | Novak et al. | 6,334,861 | B1 | 1/2002 | Chandler et al. |
| 6,063,103 | A | 5/2000 | Hashiguchi | D453,923 | S | 2/2002 | Olson |
| 6,066,139 | A | 5/2000 | Ryan et al. | 6,345,532 | B1 | 2/2002 | Coudray et al. |
| 6,071,283 | A | 6/2000 | Nardella et al. | 6,350,264 | B1 | 2/2002 | Hooven |
| 6,074,386 | A | 6/2000 | Goble et al. | D454,951 | S | 3/2002 | Bon |
| 6,077,287 | A | 6/2000 | Taylor et al. | 6,352,536 | B1 | 3/2002 | Buysse et al. |
| 6,080,180 | A | 6/2000 | Yoon et al. | 6,358,249 | B1 | 3/2002 | Chen et al. |
| RE36,795 | E | 7/2000 | Rydell | 6,358,259 | B1 | 3/2002 | Swain et al. |
| 6,083,150 | A | 7/2000 | Aznoian et al. | 6,358,268 | B1 | 3/2002 | Hunt et al. |
| 6,083,223 | A | 7/2000 | Baker | 6,361,534 | B1 | 3/2002 | Chen et al. |
| 6,086,586 | A | 7/2000 | Hooven | 6,364,879 | B1 | 4/2002 | Chen et al. |
| 6,086,601 | A | 7/2000 | Yoon | D457,958 | S | 5/2002 | Dycus et al. |
| 6,090,107 | A | 7/2000 | Borgmeier et al. | D457,959 | S | 5/2002 | Tetzlaff et al. |
| 6,090,123 | A | 7/2000 | Culp et al. | 6,385,265 | B1 | 5/2002 | Duffy et al. |
| 6,096,037 | A | 8/2000 | Mulier et al. | 6,387,094 | B1 | 5/2002 | Eitenmuller |
| 6,099,537 | A | 8/2000 | Sugai et al. | 6,391,035 | B1 | 5/2002 | Appleby et al. |
| 6,099,550 | A | 8/2000 | Yoon | 702,472 | A1 | 6/2002 | Pignolet |
| 6,102,909 | A | 8/2000 | Chen et al. | 6,398,779 | B1 | 6/2002 | Buysse et al. |
| 6,106,542 | A | 8/2000 | Toybin et al. | 6,402,747 | B1 | 6/2002 | Lindemann et al. |
| 6,110,171 | A | 8/2000 | Rydell | 6,409,728 | B1 | 6/2002 | Ehr et al. |
| 6,113,596 | A | 9/2000 | Hooven et al. | H2037 | H | 7/2002 | Yates et al. |
| 6,113,598 | A | 9/2000 | Baker | 6,419,675 | B1 | 7/2002 | Gallo, Sr. |
| 6,117,158 | A | 9/2000 | Measamer et al. | 6,425,896 | B1 | 7/2002 | Baltschun et al. |
| 6,122,549 | A | 9/2000 | Sharkey et al. | 6,432,112 | B2 | 8/2002 | Brock et al. |
| 6,123,701 | A | 9/2000 | Nezhat | 6,440,130 | B1 | 8/2002 | Mulier et al. |
| H1904 | H | 10/2000 | Yates et al. | 6,440,144 | B1 | 8/2002 | Bacher |
| 6,126,658 | A | 10/2000 | Baker | 6,443,952 | B1 | 9/2002 | Mulier et al. |
| 6,126,665 | A | 10/2000 | Yoon | 6,443,970 | B1 | 9/2002 | Schulze et al. |
| 6,139,563 | A | 10/2000 | Cosgrove, III et al. | 6,451,018 | B1 | 9/2002 | Lands et al. |
| 6,143,005 | A | 11/2000 | Yoon et al. | 6,458,125 | B1 | 10/2002 | Cosmescu |
| 6,152,923 | A | 11/2000 | Ryan | 6,458,128 | B1 | 10/2002 | Schulze |
| 6,152,924 | A | 11/2000 | Parins | 6,458,129 | B2 | 10/2002 | Scarfi |
| 6,159,217 | A | 12/2000 | Robie et al. | 6,458,130 | B1 | 10/2002 | Frazier et al. |
| 6,162,220 | A | 12/2000 | Nezhat | 6,461,352 | B2 | 10/2002 | Morgan et al. |
| 6,171,316 | B1 | 1/2001 | Kovac et al. | 6,461,368 | B2 | 10/2002 | Fogarty et al. |
| 6,174,309 | B1 | 1/2001 | Wrublewski et al. | 6,464,701 | B1 | 10/2002 | Hooven et al. |
| 6,174,310 | B1 | 1/2001 | Kirwan, Jr. | 6,464,702 | B2 | 10/2002 | Schulze et al. |
| 6,178,628 | B1 | 1/2001 | Clemens et al. | 6,464,704 | B2 | 10/2002 | Schmaltz et al. |
| 6,179,834 | B1 | 1/2001 | Buysse et al. | 6,471,696 | B1 | 10/2002 | Berube et al. |
| 6,179,837 | B1 | 1/2001 | Hooven | D465,281 | S | 11/2002 | Lang |
| 6,183,467 | B1 | 2/2001 | Shapeton et al. | D466,209 | S | 11/2002 | Bon |
| 6,187,003 | B1 | 2/2001 | Buysse et al. | 6,485,489 | B2 | 11/2002 | Teirstein et al. |
| 6,190,386 | B1 | 2/2001 | Rydell | 6,488,680 | B1 | 12/2002 | Francischelli et al. |
| 6,190,400 | B1 | 2/2001 | VanDeMoer et al. | 6,494,888 | B1 | 12/2002 | Laufer et al. |
| 6,193,709 | B1 | 2/2001 | Miyawaki et al. | 6,500,176 | B1 | 12/2002 | Truckai et al. |
| 6,193,718 | B1 | 2/2001 | Kortenbach et al. | 6,506,196 | B1 | 1/2003 | Laufer |
| 6,206,876 | B1 | 3/2001 | Levine et al. | 6,508,815 | B1 | 1/2003 | Strul et al. |
| 6,206,877 | B1 | 3/2001 | Kese et al. | 6,511,480 | B1 | 1/2003 | Tetzlaff et al. |
| 6,206,893 | B1 | 3/2001 | Klein et al. | 6,514,215 | B1 | 2/2003 | Ouchi |
| 6,214,028 | B1 | 4/2001 | Yoon et al. | 6,514,252 | B2 | 2/2003 | Nezhat et al. |
| 6,217,602 | B1 | 4/2001 | Redmon | 6,517,536 | B2 | 2/2003 | Hooven et al. |
| 6,217,615 | B1 | 4/2001 | Sioshansi et al. | 6,517,539 | B1 | 2/2003 | Smith et al. |
| 6,221,039 | B1 | 4/2001 | Durgin et al. | 6,527,771 | B1 | 3/2003 | Weadock et al. |
| 6,223,100 | B1 | 4/2001 | Green | 6,533,784 | B2 | 3/2003 | Truckai et al. |
| 6,224,593 | B1 | 5/2001 | Ryan et al. | 6,537,272 | B2 | 3/2003 | Christopherson et al. |
| 6,224,614 | B1 | 5/2001 | Yoon | 6,545,239 | B2 | 4/2003 | Spedale et al. |
| 6,228,080 | B1 | 5/2001 | Gines | 6,554,844 | B2 | 4/2003 | Lee et al. |
| 6,228,083 | B1 | 5/2001 | Lands et al. | 728,883 | A1 | 5/2003 | Downes |
| 6,248,124 | B1 | 6/2001 | Pedros et al. | 6,558,385 | B1 | 5/2003 | McClurken et al. |
| 6,248,944 | B1 | 6/2001 | Ito | 6,562,037 | B2 | 5/2003 | Paton et al. |
| 6,261,307 | B1 | 7/2001 | Yoon et al. | 6,569,105 | B1 | 5/2003 | Kortenbach et al. |
| 6,267,761 | B1 | 7/2001 | Ryan | 6,582,450 | B2 | 6/2003 | Ouchi |
| 6,270,497 | B1 | 8/2001 | Sekino et al. | 6,585,735 | B1 | 7/2003 | Frazier et al. |
| 6,270,508 | B1 | 8/2001 | Klieman et al. | 6,602,252 | B2 | 8/2003 | Mollenauer |
| 6,273,887 | B1 | 8/2001 | Yamauchi et al. | 6,605,790 | B2 | 8/2003 | Yoshida |
| 6,277,117 | B1 | 8/2001 | Tetzlaff et al. | 6,610,060 | B2 | 8/2003 | Mulier et al. |
| 6,280,458 | B1 | 8/2001 | Boche et al. | 6,613,048 | B2 | 9/2003 | Mulier et al. |
| 6,283,961 | B1 | 9/2001 | Underwood et al. | 6,616,654 | B2 | 9/2003 | Mollenauer |
| D449,886 | S | 10/2001 | Tetzlaff et al. | 6,616,658 | B2 | 9/2003 | Ineson |
| 6,298,550 | B1 | 10/2001 | Kirwan | 6,616,661 | B2 | 9/2003 | Wellman et al. |
| 6,302,424 | B1 | 10/2001 | Gisinger et al. | 6,620,161 | B2 | 9/2003 | Schulze et al. |

| | | |
|---|---|---|
| 6,620,184 B2 | 9/2003 | De Laforcade et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| 496,997 A1 | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 * | 8/2006 | Couture et al. ............... 606/51 |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 * | 9/2006 | Sartor et al. ............... 29/11 |
| 7,107,124 B2 | 9/2006 | Green |
| 7,108,694 B2 | 9/2006 | Miura et al. |
| 7,112,199 B2 | 9/2006 | Cosmescu |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| D538,932 S | 3/2007 | Malik |

| Patent | Type | Date | Inventor |
|---|---|---|---|
| 7,189,233 | B2 | 3/2007 | Truckai et al. |
| 7,195,631 | B2 | 3/2007 | Dumbauld |
| D541,418 | S | 4/2007 | Schechter et al. |
| 7,204,835 | B2 | 4/2007 | Latterell et al. |
| 7,207,990 | B2 | 4/2007 | Lands et al. |
| 7,208,005 | B2 | 4/2007 | Frecker et al. |
| D541,611 | S | 5/2007 | Aglassinge |
| D541,938 | S | 5/2007 | Kerr et al |
| 7,211,084 | B2 | 5/2007 | Goble et al. |
| 7,223,264 | B2 | 5/2007 | Daniel et al. |
| 7,223,265 | B2 | 5/2007 | Keppel |
| D545,432 | S | 6/2007 | Watanabe |
| 7,232,440 | B2 | 6/2007 | Dumbauld et al. |
| D547,154 | S | 7/2007 | Lee |
| 7,238,184 | B2 | 7/2007 | Megerman et al. |
| 7,241,288 | B2 | 7/2007 | Braun |
| 7,241,296 | B2 | 7/2007 | Buysse et al. |
| 7,244,257 | B2 | 7/2007 | Podhajsky et al. |
| 7,246,734 | B2 | 7/2007 | Shelton, IV |
| 7,248,944 | B2 | 7/2007 | Green |
| 7,252,667 | B2 | 8/2007 | Moses et al. |
| 7,255,697 | B2 | 8/2007 | Dycus et al. |
| 7,267,677 | B2 | 9/2007 | Johnson et al. |
| 7,270,660 | B2 | 9/2007 | Ryan |
| 7,270,664 | B2 | 9/2007 | Johnson et al. |
| 7,276,068 | B2 | 10/2007 | Johnson et al. |
| 7,291,161 | B2 | 11/2007 | Hooven |
| 7,300,435 | B2 | 11/2007 | Wham et al. |
| 7,303,557 | B2 | 12/2007 | Wham et al. |
| 7,311,709 | B2 | 12/2007 | Truckai et al. |
| 7,314,471 | B2 | 1/2008 | Holman |
| 7,318,823 | B2 | 1/2008 | Sharps et al. |
| 7,326,202 | B2 | 2/2008 | McGaffigan |
| 7,329,256 | B2 | 2/2008 | Johnson et al. |
| 7,329,257 | B2 | 2/2008 | Kanehira et al. |
| D564,662 | S | 3/2008 | Moses et al. |
| 7,338,526 | B2 | 3/2008 | Steinberg |
| 7,342,754 | B2 | 3/2008 | Fitzgerald et al. |
| 7,344,268 | B2 | 3/2008 | Jhigamian |
| 7,347,864 | B2 | 3/2008 | Vargas |
| D567,943 | S | 4/2008 | Moses et al. |
| 7,354,440 | B2 | 4/2008 | Truckal et al. |
| 7,367,976 | B2 | 5/2008 | Lawes et al. |
| 7,377,920 | B2 | 5/2008 | Buysse et al. |
| 7,384,420 | B2 | 6/2008 | Dycus et al. |
| 7,384,421 | B2 | 6/2008 | Hushka |
| 7,396,265 | B2 | 7/2008 | Darley et al. |
| 7,396,336 | B2 | 7/2008 | Orszulak et al. |
| 7,396,356 | B2 | 7/2008 | Mollenauer |
| D575,395 | S | 8/2008 | Hushka |
| D575,401 | S | 8/2008 | Hixson et al. |
| 7,425,835 | B2 | 9/2008 | Eisele |
| 7,431,721 | B2 | 10/2008 | Paton et al. |
| 7,435,249 | B2 | 10/2008 | Buysse et al. |
| 7,442,193 | B2 | 10/2008 | Shields et al. |
| 7,442,194 | B2 | 10/2008 | Dumbauld et al. |
| 7,445,621 | B2 | 11/2008 | Dumbauld et al. |
| D582,038 | S | 12/2008 | Swoyer et al. |
| 7,458,972 | B2 | 12/2008 | Keppel |
| 7,473,253 | B2 | 1/2009 | Dycus et al. |
| 7,481,810 | B2 | 1/2009 | Dumbauld et al. |
| 7,487,780 | B2 | 2/2009 | Hooven |
| 7,491,201 | B2 | 2/2009 | Shields et al. |
| 7,491,202 | B2 | 2/2009 | Odom et al. |
| 7,500,975 | B2 | 3/2009 | Cunningham et al. |
| 7,503,474 | B2 | 3/2009 | Hillstead et al. |
| 7,510,556 | B2 | 3/2009 | Nguyen et al. |
| 7,513,898 | B2 | 4/2009 | Johnson et al. |
| 7,517,351 | B2 | 4/2009 | Culp et al. |
| 7,540,872 | B2 | 6/2009 | Schechter et al. |
| 7,549,995 | B2 | 6/2009 | Schultz |
| 7,553,312 | B2 | 6/2009 | Tetzlaff et al. |
| 7,582,087 | B2 | 9/2009 | Tetzlaff et al. |
| 7,588,565 | B2 | 9/2009 | Marchitto et al. |
| 7,594,313 | B2 | 9/2009 | Prakash et al. |
| 7,594,916 | B2 | 9/2009 | Weinberg |
| 7,597,693 | B2 | 10/2009 | Garrison |
| 7,621,910 | B2 | 11/2009 | Sugi |
| 7,624,186 | B2 | 11/2009 | Tanida |
| 7,628,791 | B2 | 12/2009 | Garrison et al. |
| 7,628,792 | B2 | 12/2009 | Guerra |
| 7,637,409 | B2 | 12/2009 | Marczyk |
| 7,641,653 | B2 | 1/2010 | Dalla Betta et al. |
| 7,651,493 | B2 | 1/2010 | Arts et al. |
| 7,651,494 | B2 | 1/2010 | McClurken et al. |
| 7,655,007 | B2 | 2/2010 | Baily |
| 7,668,597 | B2 | 2/2010 | Engmark et al. |
| 7,678,111 | B2 | 3/2010 | Mulier et al. |
| 7,686,804 | B2 | 3/2010 | Johnson et al. |
| 7,686,827 | B2 | 3/2010 | Hushka |
| 7,708,735 | B2 | 5/2010 | Chapman et al. |
| 7,717,115 | B2 | 5/2010 | Barrett et al. |
| 7,717,904 | B2 | 5/2010 | Suzuki et al. |
| 7,717,914 | B2 | 5/2010 | Kimura |
| 7,717,915 | B2 | 5/2010 | Miyazawa |
| 7,722,607 | B2 | 5/2010 | Dumbauld et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| 7,731,717 | B2 | 6/2010 | Odom et al. |
| 7,736,374 | B2 | 6/2010 | Vaughan et al. |
| 7,744,615 | B2 | 6/2010 | Couture |
| 7,749,217 | B2 | 7/2010 | Podhajsky |
| 7,753,908 | B2 | 7/2010 | Swanson |
| 7,753,909 | B2 | 7/2010 | Chapman et al. |
| D621,503 | S | 8/2010 | Otten et al. |
| 7,766,910 | B2 | 8/2010 | Hixson et al. |
| 7,771,425 | B2 | 8/2010 | Dycus et al. |
| 7,776,036 | B2 | 8/2010 | Schechter et al. |
| 7,776,037 | B2 | 8/2010 | Odom |
| 7,780,662 | B2 | 8/2010 | Bahney |
| 7,780,663 | B2 | 8/2010 | Yates et al. |
| 7,789,878 | B2 | 9/2010 | Dumbauld et al. |
| 7,799,026 | B2 | 9/2010 | Schechter et al. |
| 7,799,028 | B2 | 9/2010 | Schechter et al. |
| 7,811,283 | B2 | 10/2010 | Moses et al. |
| 7,819,872 | B2 | 10/2010 | Johnson et al. |
| D627,462 | S | 11/2010 | Kingsley |
| D628,289 | S | 11/2010 | Romero |
| D628,290 | S | 11/2010 | Romero |
| 7,828,798 | B2 | 11/2010 | Buysse et al. |
| 7,832,408 | B2 | 11/2010 | Shelton, IV et al. |
| 7,837,685 | B2 | 11/2010 | Weinberg et al. |
| 7,839,674 | B2 | 11/2010 | Lowrey et al. |
| 7,842,033 | B2 | 11/2010 | Isaacson et al. |
| 7,846,158 | B2 | 12/2010 | Podhajsky |
| 7,846,161 | B2 | 12/2010 | Dumbauld et al. |
| 7,857,812 | B2 | 12/2010 | Dycus et al. |
| D630,324 | S | 1/2011 | Reschke |
| 7,877,852 | B2 | 2/2011 | Unger et al. |
| 7,877,853 | B2 | 2/2011 | Unger et al. |
| 7,879,035 | B2 | 2/2011 | Garrison et al. |
| 7,887,535 | B2 | 2/2011 | Lands et al. |
| 7,887,536 | B2 | 2/2011 | Johnson et al. |
| 7,896,878 | B2 | 3/2011 | Johnson et al. |
| 7,898,288 | B2 | 3/2011 | Wong |
| 7,900,805 | B2 | 3/2011 | Shelton, IV et al. |
| 7,901,400 | B2 | 3/2011 | Wham et al. |
| 7,905,380 | B2 | 3/2011 | Shelton, IV et al. |
| 7,909,820 | B2 | 3/2011 | Lipson et al. |
| 7,909,823 | B2 | 3/2011 | Moses et al. |
| 7,922,718 | B2 | 4/2011 | Moses et al. |
| 7,922,953 | B2 * | 4/2011 | Guerra .................. 264/272.11 |
| 7,931,649 | B2 | 4/2011 | Couture et al. |
| 7,935,052 | B2 | 5/2011 | Dumbauld |
| 7,945,332 | B2 | 5/2011 | Schechter |
| 7,947,041 | B2 | 5/2011 | Tetzlaff et al. |
| 7,951,149 | B2 | 5/2011 | Carlton |
| 7,951,150 | B2 | 5/2011 | Johnson et al. |
| 7,955,332 | B2 | 6/2011 | Arts et al. |
| 7,963,965 | B2 | 6/2011 | Buysse et al. |
| 7,967,839 | B2 | 6/2011 | Flock et al. |
| 7,972,328 | B2 | 7/2011 | Wham et al. |
| 7,976,544 | B2 | 7/2011 | McClurken et al. |
| 2002/0107517 | A1 | 8/2002 | Witt et al. |
| 2002/0111624 | A1 | 8/2002 | Witt et al. |

| | | | | | | |
|---|---|---|---|---|---|---|
| 2002/0165469 A1 | 11/2002 | Murakami | | 2008/0281311 A1 | 11/2008 | Dunning et al. |
| 2003/0014052 A1 | 1/2003 | Buysse et al. | | 2008/0300580 A1 | 12/2008 | Shelton, IV et al. |
| 2003/0014053 A1 | 1/2003 | Nguyen et al. | | 2008/0312653 A1 | 12/2008 | Arts et al. |
| 2003/0018332 A1 | 1/2003 | Schmaltz et al. | | 2008/0319442 A1 | 12/2008 | Unger et al. |
| 2003/0069570 A1 | 4/2003 | Witzel et al. | | 2009/0012520 A1 | 1/2009 | Hixson et al. |
| 2003/0109875 A1 | 6/2003 | Tetzlaff et al. | | 2009/0012556 A1 | 1/2009 | Boudreaux et al. |
| 2003/0114851 A1 | 6/2003 | Truckai et al. | | 2009/0015832 A1 | 1/2009 | Popovic et al. |
| 2003/0130653 A1 | 7/2003 | Sixto, Jr. et al. | | 2009/0024126 A1 | 1/2009 | Artale et al. |
| 2003/0139741 A1 | 7/2003 | Goble et al. | | 2009/0036881 A1 | 2/2009 | Artale et al. |
| 2003/0158548 A1 | 8/2003 | Phan et al. | | 2009/0036899 A1 | 2/2009 | Carlton et al. |
| 2003/0171747 A1 | 9/2003 | Kanehira et al. | | 2009/0043304 A1 | 2/2009 | Tetzlaff et al. |
| 2003/0181910 A1 | 9/2003 | Dycus et al. | | 2009/0048596 A1 | 2/2009 | Shields et al. |
| 2003/0191396 A1 | 10/2003 | Sanghvi et al. | | 2009/0062794 A1 | 3/2009 | Buysse et al. |
| 2003/0216732 A1 | 11/2003 | Truckai et al. | | 2009/0065565 A1 | 3/2009 | Cao |
| 2003/0229344 A1 | 12/2003 | Dycus et al. | | 2009/0076534 A1 | 3/2009 | Shelton, IV et al. |
| 2003/0236325 A1 | 12/2003 | Bonora | | 2009/0082766 A1 | 3/2009 | Unger et al. |
| 2004/0030330 A1 | 2/2004 | Brassell et al. | | 2009/0088738 A1 | 4/2009 | Guerra et al. |
| 2004/0064151 A1 | 4/2004 | Mollenauer | | 2009/0088739 A1 | 4/2009 | Hushka et al. |
| 2004/0073238 A1 | 4/2004 | Makower | | 2009/0088740 A1 | 4/2009 | Guerra et al. |
| 2004/0073256 A1 | 4/2004 | Marchitto et al. | | 2009/0088741 A1 | 4/2009 | Hushka et al. |
| 2004/0115296 A1 | 6/2004 | Duffin | | 2009/0088744 A1 | 4/2009 | Townsend |
| 2004/0176779 A1 | 9/2004 | Casutt et al. | | 2009/0088745 A1 | 4/2009 | Hushka et al. |
| 2004/0199181 A1 | 10/2004 | Knodel et al. | | 2009/0088746 A1 | 4/2009 | Hushka et al. |
| 2004/0224590 A1 | 11/2004 | Rawa et al. | | 2009/0088747 A1 | 4/2009 | Hushka et al. |
| 2004/0236326 A1 | 11/2004 | Schulze et al. | | 2009/0088748 A1 | 4/2009 | Guerra et al. |
| 2004/0249374 A1 | 12/2004 | Tetzlaff et al. | | 2009/0088749 A1 | 4/2009 | Hushka et al. |
| 2004/0260281 A1 | 12/2004 | Baxter, III et al. | | 2009/0088750 A1 | 4/2009 | Hushka et al. |
| 2005/0004564 A1 | 1/2005 | Wham et al. | | 2009/0105750 A1 | 4/2009 | Price et al. |
| 2005/0004569 A1 | 1/2005 | Witt et al. | | 2009/0112200 A1 | 4/2009 | Eggers |
| 2005/0033278 A1 | 2/2005 | McClurken et al. | | 2009/0112206 A1 | 4/2009 | Dumbauld et al. |
| 2005/0059858 A1 | 3/2005 | Frith et al. | | 2009/0131934 A1 | 5/2009 | Odom et al. |
| 2005/0059934 A1 | 3/2005 | Wenchell et al. | | 2009/0138006 A1 | 5/2009 | Bales et al. |
| 2005/0096645 A1 | 5/2005 | Wellman et al. | | 2009/0149853 A1 | 6/2009 | Shields et al. |
| 2005/0149017 A1 | 7/2005 | Dycus | | 2009/0149854 A1 | 6/2009 | Cunningham et al. |
| 2005/0254081 A1 | 11/2005 | Ryu et al. | | 2009/0157071 A1 | 6/2009 | Wham et al. |
| 2005/0283148 A1 | 12/2005 | Janssen et al. | | 2009/0157072 A1 | 6/2009 | Wham et al. |
| 2006/0052779 A1 | 3/2006 | Hammill | | 2009/0157075 A1 | 6/2009 | Wham et al. |
| 2006/0064086 A1 | 3/2006 | Odom | | 2009/0171350 A1 | 7/2009 | Dycus et al. |
| 2006/0079933 A1 | 4/2006 | Hushka et al. | | 2009/0171354 A1 | 7/2009 | Deville et al. |
| 2006/0084973 A1 | 4/2006 | Hushka | | 2009/0177094 A1 | 7/2009 | Brown et al. |
| 2006/0173452 A1 | 8/2006 | Buysse et al. | | 2009/0182327 A1 | 7/2009 | Unger |
| 2006/0190035 A1 | 8/2006 | Hushka et al. | | 2009/0182329 A1 | 7/2009 | Dycus |
| 2006/0217709 A1 | 9/2006 | Couture et al. | | 2009/0187188 A1 | 7/2009 | Guerra et al. |
| 2006/0253126 A1 | 11/2006 | Bjerken et al. | | 2009/0198233 A1 | 8/2009 | Chojin |
| 2006/0259036 A1 | 11/2006 | Tetzlaff et al. | | 2009/0204114 A1 | 8/2009 | Odom |
| 2006/0264922 A1 | 11/2006 | Sartor et al. | | 2009/0209957 A1 | 8/2009 | Schmaltz et al. |
| 2006/0283093 A1 | 12/2006 | Petrovic et al. | | 2009/0209960 A1 | 8/2009 | Chojin |
| 2006/0287641 A1 | 12/2006 | Perlin | | 2009/0234354 A1 | 9/2009 | Johnson et al. |
| 2007/0043337 A1 | 2/2007 | McAuley | | 2009/0248021 A1 | 10/2009 | Mckenna |
| 2007/0043353 A1 | 2/2007 | Dycus et al. | | 2009/0254081 A1 | 10/2009 | Allison et al. |
| 2007/0062017 A1 | 3/2007 | Dycus et al. | | 2009/0261804 A1 | 10/2009 | McKenna et al. |
| 2007/0118115 A1 | 5/2007 | Artale et al. | | 2009/0292282 A9 | 11/2009 | Dycus |
| 2007/0173811 A1 | 7/2007 | Couture et al. | | 2009/0318912 A1 | 12/2009 | Mayer et al. |
| 2007/0173813 A1 | 7/2007 | Odom | | 2010/0016857 A1 | 1/2010 | McKenna et al. |
| 2007/0198011 A1 | 8/2007 | Sugita | | 2010/0023009 A1 | 1/2010 | Moses et al. |
| 2007/0225695 A1 | 9/2007 | Mayer et al. | | 2010/0036375 A1 | 2/2010 | Regadas |
| 2007/0255279 A1 | 11/2007 | Buysse et al. | | 2010/0042140 A1 | 2/2010 | Cunningham |
| 2007/0260238 A1 | 11/2007 | Guerra | | 2010/0042142 A1 | 2/2010 | Cunningham |
| 2007/0260242 A1 | 11/2007 | Dycus et al. | | 2010/0042143 A1 | 2/2010 | Cunningham |
| 2007/0265616 A1 | 11/2007 | Couture et al. | | 2010/0049187 A1 | 2/2010 | Carlton et al. |
| 2007/0265620 A1 | 11/2007 | Kraas et al. | | 2010/0057081 A1 | 3/2010 | Hanna |
| 2008/0004616 A1 | 1/2008 | Patrick | | 2010/0057082 A1 | 3/2010 | Hanna |
| 2008/0015575 A1 | 1/2008 | Odom et al. | | 2010/0057083 A1 | 3/2010 | Hanna |
| 2008/0033428 A1 | 2/2008 | Artale et al. | | 2010/0057084 A1 | 3/2010 | Hanna |
| 2008/0039831 A1 | 2/2008 | Odom et al. | | 2010/0063500 A1 | 3/2010 | Muszala |
| 2008/0039835 A1 | 2/2008 | Johnson et al. | | 2010/0069903 A1 | 3/2010 | Allen, IV et al. |
| 2008/0045947 A1 | 2/2008 | Johnson et al. | | 2010/0069904 A1 | 3/2010 | Cunningham |
| 2008/0058802 A1 | 3/2008 | Couture et al. | | 2010/0069953 A1 | 3/2010 | Cunningham et al. |
| 2008/0082100 A1 | 4/2008 | Orton et al. | | 2010/0076427 A1 | 3/2010 | Heard |
| 2008/0125767 A1 | 5/2008 | Blaha | | 2010/0076430 A1 | 3/2010 | Romero |
| 2008/0125797 A1 | 5/2008 | Kelleher | | 2010/0076431 A1 | 3/2010 | Allen, IV |
| 2008/0208289 A1 | 8/2008 | Darley et al. | | 2010/0076432 A1 | 3/2010 | Horner |
| 2008/0215050 A1 | 9/2008 | Bakos | | 2010/0087816 A1 | 4/2010 | Roy |
| 2008/0234701 A1 | 9/2008 | Morales et al. | | 2010/0087818 A1 | 4/2010 | Cunningham |
| 2008/0243120 A1 | 10/2008 | Lawes et al. | | 2010/0094271 A1 | 4/2010 | Ward et al. |
| 2008/0243158 A1 | 10/2008 | Morgan | | 2010/0094286 A1 | 4/2010 | Chojin |
| 2008/0249523 A1 | 10/2008 | McPherson et al. | | 2010/0094287 A1 | 4/2010 | Cunningham et al. |
| 2008/0249527 A1 | 10/2008 | Couture | | 2010/0100122 A1 | 4/2010 | Hinton |
| 2008/0271360 A1 | 11/2008 | Barfield | | 2010/0130971 A1 | 5/2010 | Baily |

| | | | | | |
|---|---|---|---|---|---|
| 2010/0130977 A1 | 5/2010 | Garrison et al. | DE | 20 2007 016233 | 3/2008 |
| 2010/0145334 A1 | 6/2010 | Olson et al. | DE | 19738457 | 1/2009 |
| 2010/0179539 A1 | 7/2010 | Nau, Jr. | DE | 10 2008 018406 | 7/2009 |
| 2010/0179543 A1 | 7/2010 | Johnson et al. | EP | 0364216 | 4/1990 |
| 2010/0179545 A1 | 7/2010 | Twomey et al. | EP | 0467501 | 1/1992 |
| 2010/0179546 A1 | 7/2010 | Cunningham | EP | 0509670 | 10/1992 |
| 2010/0179547 A1 | 7/2010 | Cunningham et al. | EP | 0518230 | 12/1992 |
| 2010/0198248 A1 | 8/2010 | Vakharia | EP | 0541930 | 5/1993 |
| 2010/0204697 A1 | 8/2010 | Dumbauld et al. | EP | 0306123 | 8/1993 |
| 2010/0204698 A1 | 8/2010 | Chapman et al. | EP | 0572131 | 12/1993 |
| 2010/0217258 A1 | 8/2010 | Floume et al. | EP | 0584787 | 3/1994 |
| 2010/0217264 A1 | 8/2010 | Odom et al. | EP | 0589453 | 3/1994 |
| 2010/0249769 A1 | 9/2010 | Nau, Jr. et al. | EP | 0589555 | 3/1994 |
| 2010/0249776 A1 | 9/2010 | Kerr | EP | 0623316 | 11/1994 |
| 2010/0256635 A1 | 10/2010 | McKenna et al. | EP | 0624348 | 11/1994 |
| 2010/0274244 A1 | 10/2010 | Heard | EP | 0648475 | 4/1995 |
| 2010/0280511 A1 | 11/2010 | Rachlin et al. | EP | 0650701 | 5/1995 |
| 2010/0280515 A1 | 11/2010 | Hixson et al. | EP | 0694290 | 3/1996 |
| 2010/0286691 A1 | 11/2010 | Kerr et al. | EP | 0717966 | 6/1996 |
| 2010/0307934 A1 | 12/2010 | Chowaniec et al. | EP | 0754437 | 3/1997 |
| 2010/0312235 A1 | 12/2010 | Bahney | EP | 0517243 | 9/1997 |
| 2010/0312238 A1 | 12/2010 | Schechter et al. | EP | 0853922 | 7/1998 |
| 2010/0312242 A1 | 12/2010 | Odom | EP | 0875209 | 11/1998 |
| 2010/0331839 A1 | 12/2010 | Schechter et al. | EP | 0878169 | 11/1998 |
| 2011/0004209 A1 | 1/2011 | Lawes et al. | EP | 0887046 | 1/1999 |
| 2011/0004210 A1 | 1/2011 | Johnson et al. | EP | 0923907 | 6/1999 |
| 2011/0009864 A1 | 1/2011 | Bucciaglia et al. | EP | 0950378 | 10/1999 |
| 2011/0015632 A1 | 1/2011 | Artale | EP | 0986990 | 3/2000 |
| 2011/0018164 A1 | 1/2011 | Sartor et al. | EP | 1034747 | 9/2000 |
| 2011/0034918 A1 | 2/2011 | Reschke | EP | 1034748 | 9/2000 |
| 2011/0036183 A1 | 2/2011 | Artale et al. | EP | 1025807 | 10/2000 |
| 2011/0046623 A1 | 2/2011 | Reschke | EP | 1034746 | 10/2000 |
| 2011/0054467 A1 | 3/2011 | Mueller et al. | EP | 1050278 | 11/2000 |
| 2011/0054468 A1 | 3/2011 | Dycus | EP | 1053719 | 11/2000 |
| 2011/0054469 A1 | 3/2011 | Kappus et al. | EP | 1053720 | 11/2000 |
| 2011/0054471 A1 | 3/2011 | Gerhardt et al. | EP | 1055399 | 11/2000 |
| 2011/0054472 A1 | 3/2011 | Romero | EP | 1055400 | 11/2000 |
| 2011/0060333 A1 | 3/2011 | Mueller | EP | 1080694 | 3/2001 |
| 2011/0060334 A1 | 3/2011 | Brandt et al. | EP | 1082944 | 3/2001 |
| 2011/0060335 A1 | 3/2011 | Harper et al. | EP | 1159926 | 12/2001 |
| 2011/0060356 A1 | 3/2011 | Reschke et al. | EP | 1177771 | 2/2002 |
| 2011/0066174 A1 | 3/2011 | Gilbert | EP | 1278007 | 1/2003 |
| 2011/0071522 A1 | 3/2011 | Dumbauld et al. | EP | 1301135 | 4/2003 |
| 2011/0071523 A1 | 3/2011 | Dickhans | EP | 1330991 | 7/2003 |
| 2011/0071525 A1 | 3/2011 | Dumbauld et al. | EP | 1486177 | 6/2004 |
| 2011/0072638 A1 | 3/2011 | Brandt et al. | EP | 1472984 | 11/2004 |
| 2011/0073246 A1 | 3/2011 | Brandt et al. | EP | 0774232 | 1/2005 |
| 2011/0073594 A1 | 3/2011 | Bonn | EP | 1527747 | 5/2005 |
| 2011/0077648 A1 | 3/2011 | Lee et al. | EP | 1530952 | 5/2005 |
| 2011/0077649 A1 | 3/2011 | Kingsley | EP | 1532932 | 5/2005 |
| 2011/0082457 A1 | 4/2011 | Kerr et al. | EP | 1535581 | 6/2005 |
| 2011/0082494 A1 | 4/2011 | Kerr et al. | EP | 1609430 | 12/2005 |
| 2011/0087221 A1 | 4/2011 | Siebrecht et al. | EP | 1201192 | 2/2006 |
| 2011/0098689 A1 | 4/2011 | Nau, Jr. et al. | EP | 1632192 | 3/2006 |
| 2011/0106079 A1 | 5/2011 | Garrison et al. | EP | 1186274 | 4/2006 |
| 2011/0118736 A1 | 5/2011 | Harper et al. | EP | 1642543 | 4/2006 |
| 2011/0162796 A1 | 7/2011 | Guerra | EP | 1645238 | 4/2006 |
| | | | EP | 1645240 | 4/2006 |
| FOREIGN PATENT DOCUMENTS | | | EP | 1649821 | 4/2006 |
| CA | 2 520 413 | 3/2007 | EP | 1707143 | 10/2006 |
| CN | 201299462 | 9/2009 | EP | 1545360 | 3/2007 |
| DE | 2415263 | 10/1975 | EP | 1767163 | 3/2007 |
| DE | 2514501 | 10/1976 | EP | 1769765 | 4/2007 |
| DE | 2627679 | 1/1977 | EP | 1769766 | 4/2007 |
| DE | 3423356 | 1/1986 | EP | 1772109 | 4/2007 |
| DE | 3612646 | 4/1987 | EP | 1785097 | 5/2007 |
| DE | 8712328 | 3/1988 | EP | 1785098 | 5/2007 |
| DE | 4303882 | 8/1994 | EP | 1785101 | 5/2007 |
| DE | 4403252 | 8/1995 | EP | 1787597 | 5/2007 |
| DE | 19515914 | 7/1996 | EP | 1810625 | 7/2007 |
| DE | 19506363 | 8/1996 | EP | 1810628 | 7/2007 |
| DE | 29616210 | 1/1997 | EP | 1842500 | 10/2007 |
| DE | 19608716 | 4/1997 | EP | 1878400 | 1/2008 |
| DE | 19751106 | 5/1998 | EP | 1929970 | 6/2008 |
| DE | 19751108 | 5/1999 | EP | 1958583 | 8/2008 |
| DE | 10045375 | 4/2002 | EP | 1990019 | 11/2008 |
| DE | 10 2004 026179 | 12/2005 | EP | 1683496 | 12/2008 |
| DE | 20 2007 009165 | 10/2007 | EP | 1997438 | 12/2008 |
| DE | 20 2007 009317 | 10/2007 | EP | 1997439 | 12/2008 |

| | | |
|---|---|---|
| EP | 1527744 | 2/2009 |
| EP | 2103268 | 9/2009 |
| EP | 2147649 | 1/2010 |
| EP | 2206474 | 7/2010 |
| EP | 1920725 | 10/2010 |
| EP | 2243439 | 10/2010 |
| EP | 2294998 | 3/2011 |
| EP | 2301467 | 3/2011 |
| EP | 1628586 | 7/2011 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/19681 | 10/1993 |
| WO | WO 93/21845 | 11/1993 |
| WO | WO 94/00059 | 1/1994 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 95/20360 | 8/1995 |
| WO | WO 96/05776 | 2/1996 |
| WO | WO 96/11635 | 4/1996 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/18768 | 5/1997 |
| WO | WO 97/24073 | 7/1997 |
| WO | WO 97/24993 | 7/1997 |
| WO | WO 98/14124 | 4/1998 |
| WO | WO 98/27880 | 7/1998 |
| WO | WO 98/31290 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/25261 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/33753 | 6/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/01847 | 1/2001 |
| WO | WO 01/15614 | 3/2001 |
| WO | WO 01/17448 | 3/2001 |
| WO | WO 01/54604 | 8/2001 |
| WO | WO 02/07627 | 1/2002 |
| WO | WO 02/058544 | 8/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 02/085218 | 10/2002 |
| WO | WO 03/061500 | 7/2003 |
| WO | WO 03/090630 | 11/2003 |
| WO | WO 03/096880 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/011049 | 2/2005 |
| WO | WO 2005/030071 | 4/2005 |
| WO | WO 2005/048809 | 6/2005 |
| WO | WO 2005/050151 | 6/2005 |
| WO | WO 2005/110264 | 11/2005 |
| WO | WO 2006/021269 | 3/2006 |
| WO | WO 2008/008457 | 1/2008 |
| WO | WO 2008/040483 | 4/2008 |
| WO | WO 2008/045348 | 4/2008 |
| WO | WO 2008/045350 | 4/2008 |
| WO | WO 2008/0112147 | 9/2008 |
| WO | WO 2009/0005850 | 1/2009 |
| WO | WO 2009/0039179 | 3/2009 |
| WO | WO 2009/0039510 | 3/2009 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.

U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13,029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAU 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Intl Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Repot EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.

Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

METHOD FOR MANUFACTURING AN END EFFECTOR ASSEMBLY

CROSS-REFERENCE TO RELATED APPLICATIONS

This application is a divisional of U.S. patent application Ser. No. 11/529,414 by Paul Guerra entitled "METHOD FOR MANUFACTURING AN END EFFECTOR ASSEMBLY" filed on Sep. 28, 2006, published on Apr. 5, 2007 as U.S. Patent Application Publication US 2007/0074807 A1 entitled "METHOD FOR MANUFACTURING AN END EFFECTOR ASSEMBLY", now U.S. Pat. No. 7,922,953 issued on Apr. 12, 2011 entitled "METHOD FOR MANUFACTURING AN END EFFECTOR ASSEMBLY", and which claims the benefit of priority of U.S. Provisional Patent Application Ser. No. 60/722,186 by Paul Guerra entitled "METHOD FOR MANUFACTURING AN END EFFECTOR ASSEMBLY" filed on Sep. 30, 2005, the entire contents of each of which applications is incorporated herein by reference.

BACKGROUND

The present disclosure relates to electrosurgical instruments used for open and endoscopic surgical procedures. More particularly, the present disclosure relates to a method of manufacturing a bipolar forceps for sealing vessels and vascular tissue having an electrode assembly that is designed to enhance electrical isolation of the surface of the jaw of the forceps from an underlying strength member.

TECHNICAL FIELD

A hemostat or forceps is a simple plier-like tool that uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate tissue and/or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad that is attached externally to the patient. When the electrosurgical energy is applied, the energy travels from the active electrode, to the surgical site, through the patient and to the return electrode.

Bipolar electrosurgical forceps utilize two generally opposing electrodes that are generally disposed on the inner facing or opposing surfaces of the end effectors, which are, in turn, electrically coupled to an electrosurgical generator. Each electrode is charged to a different electric potential. Since tissue is a conductor of electrical energy, when the end effectors are utilized to clamp or grasp tissue therebetween, the electrical energy can be selectively transferred through the tissue.

Over the last several decades, more and more surgeons are complimenting traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

Certain surgical procedures require sealing blood vessels or vascular tissue. However, due to space limitations, surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

It is known that the process of coagulating small vessels is fundamentally different than vessel sealing. For the purposes herein the term "coagulation" is defined as a process of desiccating tissue wherein the tissue cells are ruptured and dried. The term "vessel sealing" is defined as the process of liquefying the collagen in the tissue so that the tissue cross-links and reforms into a fused mass. Thus, coagulation of small vessels is sufficient to close them, however, larger vessels need to be sealed to assure permanent closure.

Several journal articles have disclosed methods for sealing small blood vessels using electrosurgery. An article entitled Studies on Coagulation and the Development of an Automatic Computerized Bipolar Coagulator, Journal of Neurosurgery, Volume 75, July 1991, describes a bipolar coagulator that is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

In order to effect a proper seal with larger vessels, two predominant mechanical parameters must be accurately controlled—the pressure applied to the vessel and the gap between the electrodes, both of which affect thickness of the sealed vessel. More particularly, accurate application of the pressure may be important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness, which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical instruments have been proposed in the past for various open and endoscopic surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, sealing and cutting vessels or tissue.

Many of these instruments include blade members or shearing members that simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal. For example, it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Currently, several tissue sealing devices employ jaws that are designed as two separate parts. The jaw is first covered in an over-mold material. Then the seal plate and the covered jaw are over-molded together. As a result, this manufacturing process requires two mold tools. In addition, each part must include features by which the part can be held while the molding occurs.

SUMMARY

It is an object of the present disclosure to provide a method for manufacturing an open and/or endoscopic electrosurgical instrument in which the two separate parts of the jaws of the forceps can be molded simultaneously to save tooling costs by first disposing an insulating layer on the back of the seal plate.

It is another object of the present disclosure to provide an open and/or endoscopic electrosurgical instrument in which the covering or coating on the back of the seal plate has enhanced thermal and electrical properties for isolation as compared to the thermal and electrical properties of the plastic mold material.

More particularly, one embodiment of the present disclosure relates to a method of manufacturing a jaw member of an end effector assembly for use with an electrosurgical instrument. The method includes the steps of providing an electrically conductive tissue engaging plate and a jaw support; covering one side of the electrically conductive tissue engaging plate with an electrically insulative, thermally non-degrading coating; placing and securing the electrically conductive tissue engaging plate and the jaw support into a jaw mold; and introducing a liquid substance into the jaw mold and allowing the liquid substance to cure around the electrically conductive tissue engaging plate and the jaw support. The coating of the covering step may be of uniform thickness across the electrically conductive tissue engaging plate. In addition, the coating of the covering step may include a thickness which provides a gap-set between the electrically conductive tissue engaging plate and the jaw support during the introducing step.

One embodiment of the present disclosure relates to another method for manufacturing a jaw member of an end effector assembly for use with an electrosurgical instrument wherein the method includes the steps of: providing an electrically conductive tissue engaging plate and a jaw support; covering one side of the electrically conductive tissue engaging plate with an electrically insulative, thermally non-degrading coating; and securing the side of the electrically conductive tissue engaging plate onto the jaw support with an adhesive. The coating of the covering step may be of uniform thickness across the electrically conductive tissue engaging plate. The coating of the covering step may include a thickness which provides a gap-set between the electrically conductive tissue engaging plate and the jaw support during the introducing step.

DETAILED DESCRIPTION

It has been found that by altering the configuration of the electrode insulating material relative to the electrically conductive sealing surface, surgeons can more readily and easily produce a consistent, high quality seal and effectively reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue. It is envisioned that the configuration of the insulating material that surrounds the perimeter of the electrically conductive surface will effectively reduce current and thermal dissipation to adjacent tissue areas and generally restrict current travel to areas between the opposing electrodes. As mentioned above, this is different from dielectrically coating the outer surfaces of the instrument to prevent tissue "blanching" at points normal to the sealing site. These coatings are not designed or intended to reduce collateral tissue damage or thermal spread to adjacent tissue (tissue lying along the tissue sealing plane).

More particularly, altering the geometrical dimensions of the insulator relative to the electrically conductive surface alters the electrical path, thereby influencing the thermal spread/collateral damage to adjacent tissue structures. Preferably, the geometry of the insulating substrate also isolates the two electrically opposing poles (i.e., electrodes) from one another, thereby reducing the possibility that tissue or tissue fluids can create an unintended bridge or path for current travel. In other words, the insulator and electrically conductive sealing surface are preferably dimensioned such that the current is concentrated at the intended sealing site between the opposing electrically conductive surfaces as explained in more detail below.

Figure 1:
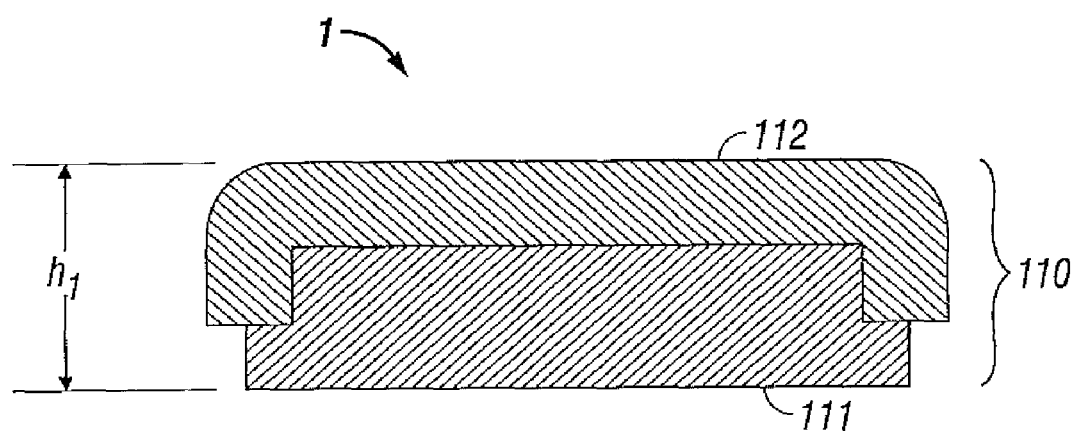
FIG. 1 is a cross-section of a prior art electrode configuration with the electrode extending over the sides of the insulator.

Referring now to FIG. 1, an electrode jaw member 110 of an end effector assembly of the prior art is shown in which an electrically conductive seal surface 112 is disposed on an electrically insulating layer 111. The electrically conductive seal surface 112 contacts tissue. The electrically conductive seal surface 112 has a width such that the electrically conductive seal surface 112 overlaps the electrically insulating layer 111. The joining process of the electrically conductive seal surface 112 and the electrically insulating layer 111 result in electrode jaw member 110 having a height "h1".

With respect to the method of manufacturing electrode jaw member 110, the jaw member 110 is first covered in an over-mold material and then the seal plate 112 and covered jaw 112 are over-molded together. The process requires two mold tools and features on each part to be held while the molding occurs.

Figure 2A:
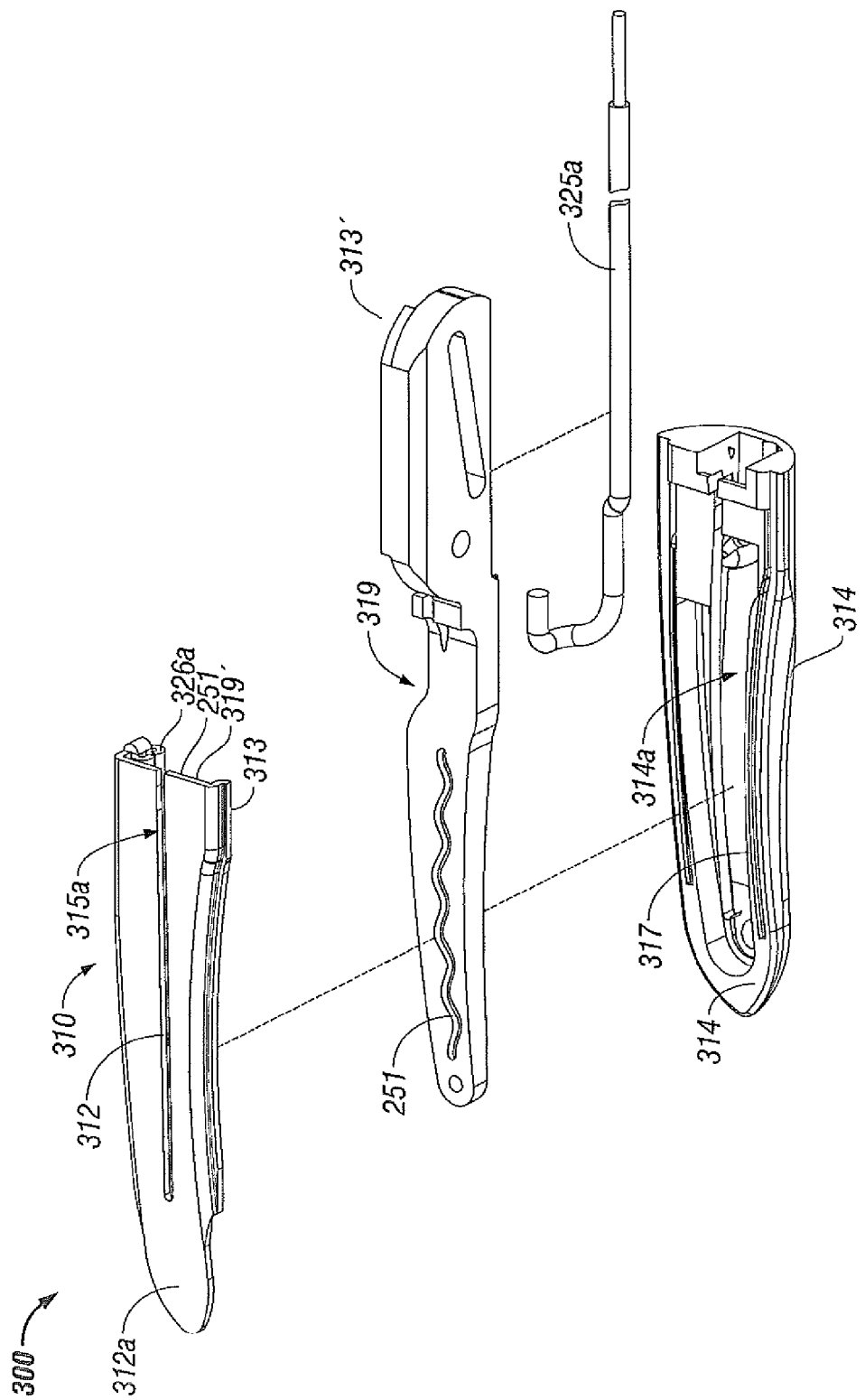
FIG. 2A is a greatly-enlarged, top perspective view of a bottom jaw member of an end effector assembly with parts separated having an insulating layer applied according to one embodiment of the present disclosure.
Figure 2B:
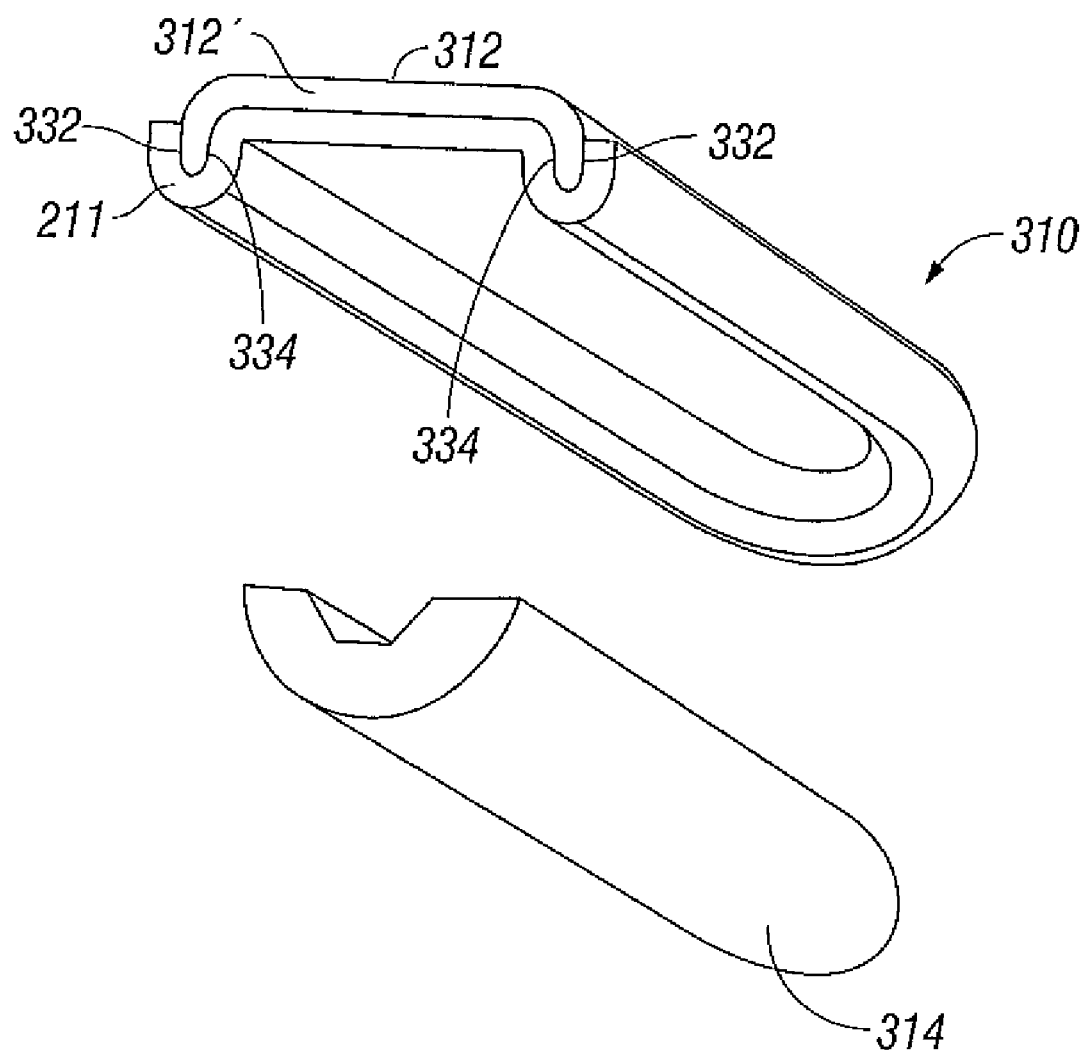
FIG. 2B is a greatly-enlarged, bottom perspective view of the bottom jaw member of an end effector assembly of FIG. 2A.

Referring to FIGS. 2A, 2B, 3A and 3B, in one embodiment of the present disclosure, as best shown in FIG. 2A, a jaw member 310 of an electrosurgical forceps may include a support base 319 which extends distally from a flange 313. The jaw member 310 includes an electrically conductive tissue engaging surface or sealing plate 312. As best shown in FIG. 2B, the electrically conductive tissue engaging sealing plate 312 has vertically-extending edges 332, 334 extending about a periphery and along a length thereof of the electrically conductive plate 312. Vertically-extending edges 332 extend externally along the electrically conductive tissue engaging surface or sealing plate 312 while vertically-extending edges 334 extend internally along an opposite side surface 312' of the electrically conductive tissue engaging surface or sealing plate 312. An electrically insulating layer 211 is disposed on the opposite side surface 312' and along the vertically-extending edges 334 that extend internally along the opposite side surface 312' and along at least a portion of the vertically-extending edges 332 that extend externally along the electrically conductive tissue engaging surface or sealing plate 312. A jaw support base 319 together with the electrically insulating layer 211 and electrically conductive tissue engaging surface 312 are encapsulated by an outer insulative housing or overmolding 314. Overmolding 314 includes a cavity 314a is dimensioned to securely engage the electrically conductive sealing surface or sealing plate 312 as well as the support base 319 and electrically insulating layer 211. Consequently, jaw member 310 has an electrically conductive sealing surface or sealing plate member 312 that is substantially surrounded by electrically insulating layer 211 and outer insulative housing or overmolding 314. The electrically conductive seal surface 312 contacts tissue.

Figure 4:
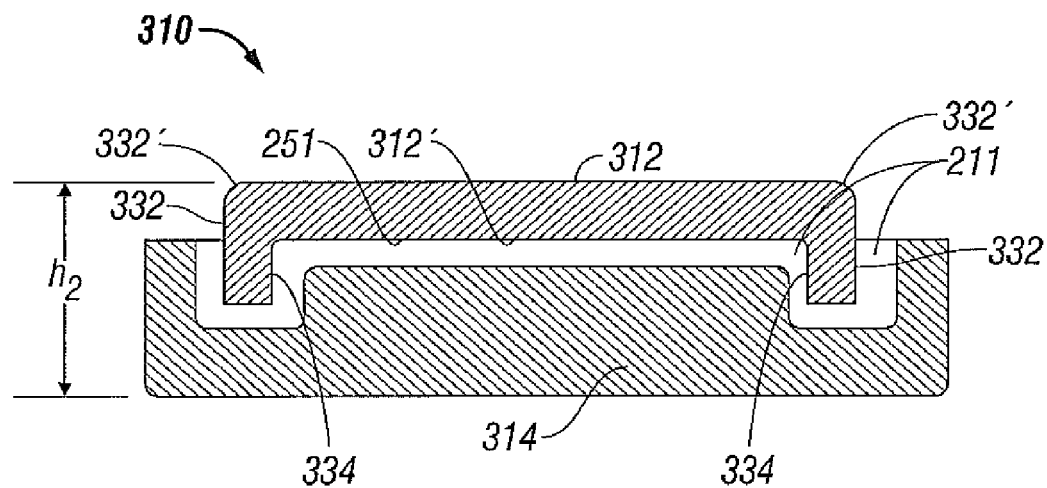
FIG. 4 is a cross-section of the electrode with an insulating layer applied to the electrode of FIGS. 2A and 2B.

For example, and as shown in FIG. 2A, the electrically conductive sealing plate 312 includes a peripheral flange 313, which surrounds the periphery of the sealing plate 312. Flange 313, is designed to matingly engage an inner lip 317 of the outer insulative housing or overmolding 314. A lead 325a extending from a circuit board (not shown) terminates within the outer insulating housing or overmolding 314 and is designed to electro-mechanically couple to the sealing plate 312 by virtue of a crimp-like connection 326a. For example, the electrically insulating layer 211 is disposed on the opposite side surface 312' and along the vertically-extending edges 334 that extend internally along the opposite side surface 312' and along at least a portion of the vertically-extending edges 332 that extend externally along the electrically conductive tissue engaging surface or sealing plate 312, electrically conductive sealing surface 312 and the outer insulating housing or overmolding 314 are preferably dimensioned to limit and/or reduce many of the known undesirable effects related to tissue sealing, e.g., flashover, thermal spread and stray current dissipation As best shown in FIG. 4, electrically conductive sealing surface 312 may also include outer peripheral edges 332' that have a pre-defined radius and the outer insulating housing or overmolding 314 meets the electrically insulating layer 211 and the electrically conductive sealing surface 312 along an adjoining edge 332 of the sealing surface 312 in a generally tangential position. At the interface, the electrically conductive surface 312 is raised relative to the outer housing 314.

Figure 3A:
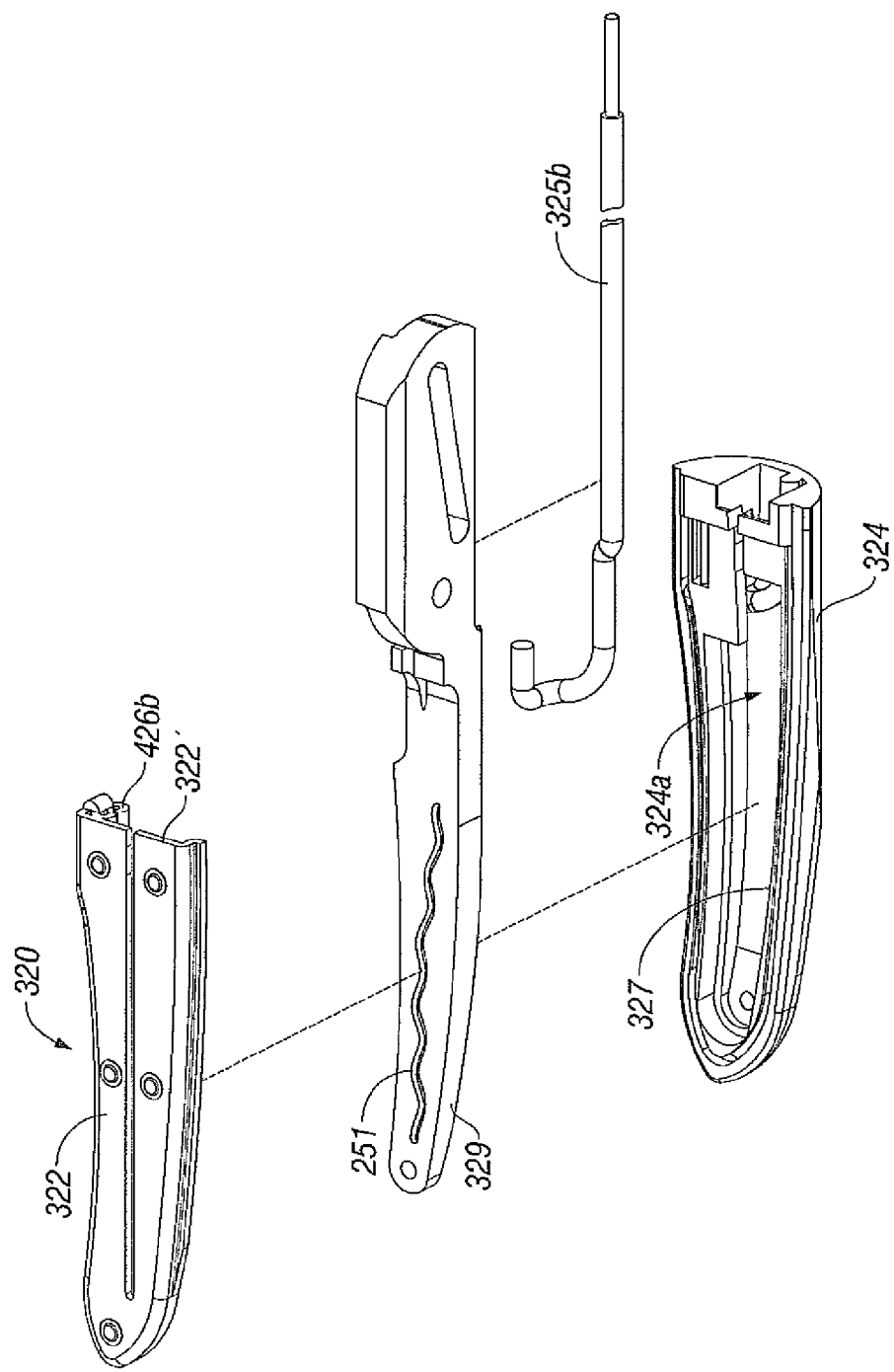
FIG. 3A is a greatly-enlarged, top perspective view of a top jaw member of an end effector assembly with parts separated having an insulating layer applied according to one embodiment of the present disclosure.
Figure 3B:
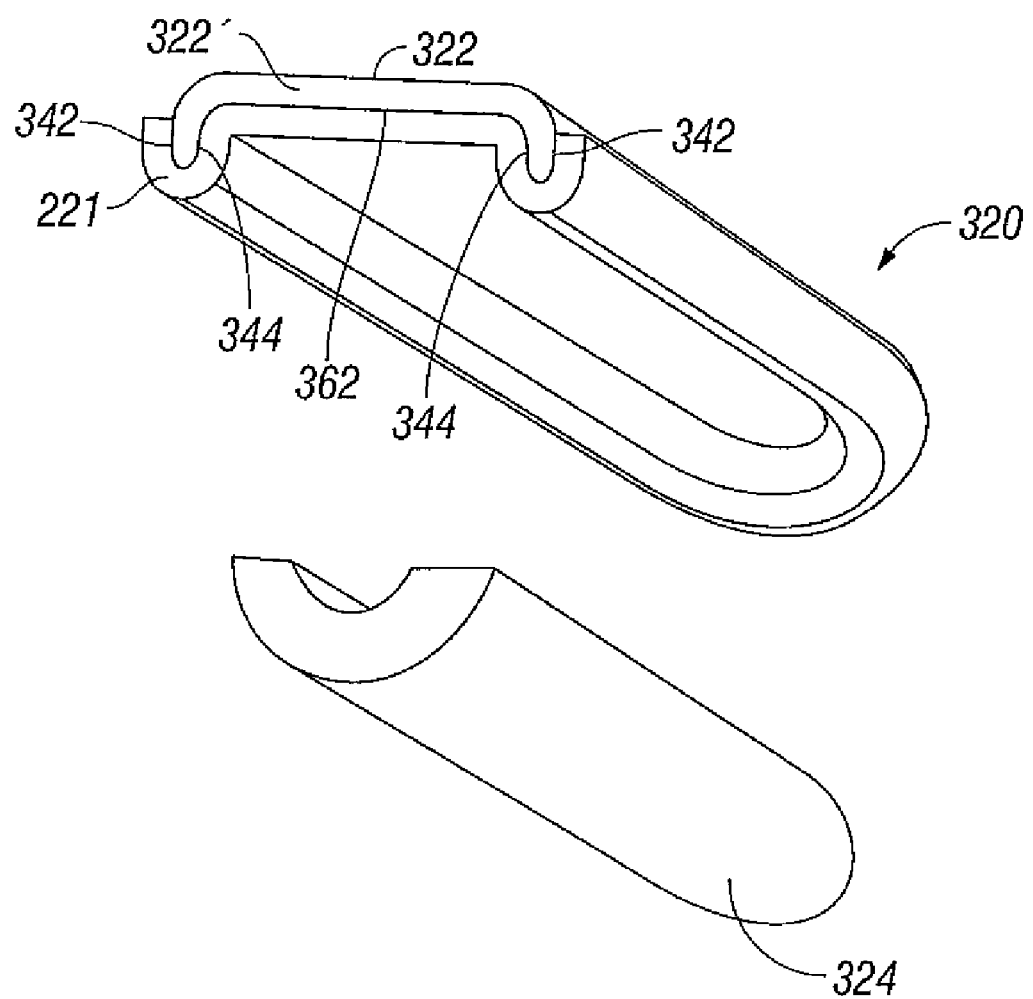
FIG. 3B is a greatly-enlarged, bottom perspective view of the jaw member of an end effector assembly of FIG. 3A.

As best illustrated in FIGS. 3A and 3B, jaw member 320 includes similar elements to jaw member 310 such as jaw insulating housing or overmolding 324, that encapsulates a support plate 329, an electrically insulating layer 221 and an electrically conductive tissue engaging sealing surface or sealing plate member 322. Similarly, the electrically conductive tissue engaging sealing plate 322 has vertically-extending edges 342, 344 extending about the periphery and along a length thereof of the electrically conductive plate 322. Vertically-extending edges 342 extend externally along the electrically conductive tissue engaging surface or sealing plate 322 while vertically-extending edges 344 extend internally along an opposite side surface 322' of the electrically conductive tissue engaging surface or sealing plate 322. The electrically conductive surface or sealing plate member 322 forms a channel 362 on the opposite side surface 322' of electrically conductive surface or sealing plate 322 such that the electrically conductive surface or sealing plate 322 and the channel 362 are dimensioned for the channel 362 to receive electrically insulating layer 221 disposed on the opposite side surface 322'.

Jaw member 320 may be assembled in a similar manner as described above with respect to jaw member 310, as described below.

Jaw members 310 and 320 are electrically isolated from one another such that electrosurgical energy can be effectively transferred through the tissue to form a tissue seal. For example, each jaw member, e.g., 310, includes a uniquely-designed electrosurgical cable path disposed therethrough that transmits electrosurgical energy to the electrically conductive sealing surface 312. Cable leads 325a and 325b, which supply power to electrode jaw members 310 and 320, respectively, are coupled to an electrosurgical generator (not shown) and are supported via support plates 319 and 329, respectively, and are held loosely but securely along the cable path to permit rotation of the jaw members 310 and 320. This configuration isolates electrically conductive sealing surface 312 from the remaining operative components of the end effector assembly 1000 or 122, jaw member 320 and shaft 12 or 109 (see FIGS. 6 and 7) and conversely isolates electrically conductive sealing surface 322 from the remaining operative components of the jaw member 310. The two electrical potentials are isolated from one another by virtue of the insulative sheathing surrounding the cable leads 325a and 325b.

FIG. 4 shows, in one embodiment, that the electrically insulating layer 211 or 221 may be made from a polymer or a polymer solution, which can be sprayed onto the opposite sides 312' and 322' of the conductive sealing surface 312 and 322, respectively. Alternatively, a ceramic material may be applied to the opposite sides 312' and 322' of electrically conductive seal plates or sealing surfaces 312 and 322 by plasma deposition or by other suitable mechanical techniques. The electrically insulating layers 211 and 221 may also be sprayed on in a uniform thickness to assure flatness.

By applying a coating of electrically insulating layer 211 and 221 onto sides 312' and 322' and vertically extending edges 332, 334 and 342, 344 of electrically conductive seal plates 312 and 322, respectively, enhanced thermal and electrical properties are provided so as to increase electrical and thermal isolation during activation, and may be dimensioned to regulate the gap distance to within a preferred gap range as described in more detail below with respect to FIG. 6. The coating of electrically insulating layer 211 and 221 may be made from a material selected from the group consisting of flame sprayed ceramic, vapor deposition polymer (parylene), an oxide layer, and an anodized coating.

In one particularly useful embodiment, overmoldings 314 and 324 are made from molded plastic material.

Figure 5:
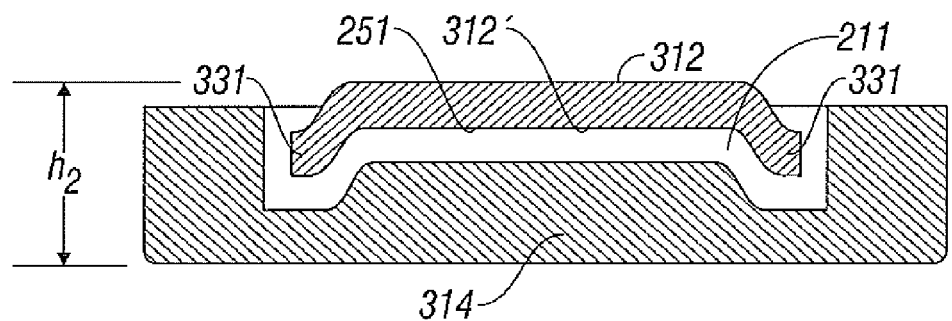
FIG. 5 is a cross-section of an overmolded stamped electrode configuration showing an insulating layer applied to the electrode of FIGS. 2A and 2B and capturing a pinch trim which depends from the electrically conductive surface.

In another particularly useful embodiment, as best illustrated in FIGS. 2, 3 and 5, the insulating layer 211 of electrode 310 is attached to seal surface 312' by applying an adhesive in an adhesive layer 251. The adhesive layer 251 may include a material that includes polyurethane or other adhesive fluids. In this case, the application of the jaw overmolding 314 is applied over the insulating layer 211 is optional. Those skilled in the art will recognize that adhesive 251 may be applied in a similar manner to the insulating layer 221 of electrode 320 and seal surface 322'. The method of manufacturing the insulating layer 211 or 221 using adhesive 251 is described below.

Figure 6:
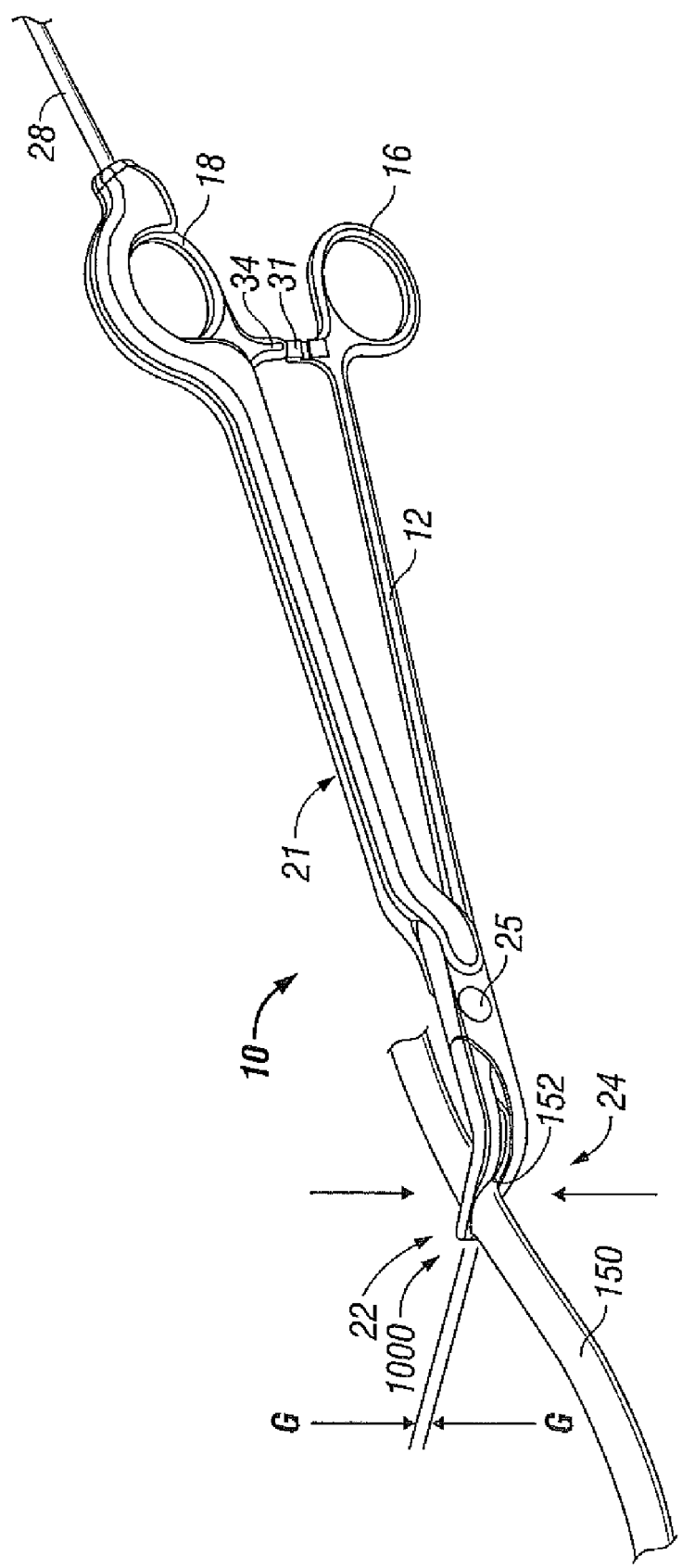
FIG. 6 is a perspective view of the open forceps of the present disclosure showing the operative motion of the forceps to effect sealing of a tubular vessel.

As mentioned above, the electrically insulating layers 211 and 221 and the overmolding 314 and 324 not only insulate the electric current but may also be dimensioned to regulate the gap distance G between the electrodes 310 and 320 when closed about tissue, which is known to contribute to the seal quality, consistency and the reduction of thermal spread across the tissue (See FIG. 6). Specifically, the coating regulates the gap set between the jaw support 319 or 329 and the plate 312 or 322 when inserted into the mold, The jaw mechanism (i.e., jaw members 310 and 320) and the coated seal surfaces 312 and 322 are held together simultaneously in a mold tool while plastic is caused to flow around the jaw members 310 and 320.

In addition, by attaching the electrically insulating layer 211 and 221 and overmolding 314 and 324 to the conductive surfaces 312' and 322', respectively, utilizing one of the above assembly techniques, the alignment and thickness, i.e., height "h2", of the electrodes 310 and 320 can be controlled. For example, and as best illustrated in comparison of FIG. 1 to FIG. 4, the overmolding manufacturing technique reduces the overall height "h2" (FIG. 4) of the electrode 310 compared to traditional manufacturing techniques, which yield a height of "h1" (FIG. 1). The smaller height "h2" allows a user access to smaller areas within the body and facilitates sealing around more delicate tissue areas.

Moreover, the overmolding technique provides more insulation, i.e., electrically insulating layers 211 and 221, along the vertically extending edges of the electrically conductive surface, which also reduces thermal spread due to less electrode to tissue contact. By dimensioning electrically insulating layer, e.g., 211 and electrode 310 in this fashion (i.e., with reduced conductive surface area), the current is restricted (i.e., concentrated) to the intended seal area rather than current being able to travel to tissue outside the seal area, which may come into contact with an outer edge of the electrode 310 (see FIG. 4). In addition, the material of the jaw overmolding 314 (and 324) provides enhanced thermal and electrical insulation properties during activation.

More particularly, the varying geometry of the electrically insulating layer 211 (and 221) and jaw overmolding 314 (and 324) compared to the electrically conductive surface 312 also isolates the two opposing poles during activation, thereby reducing the possibility that tissue or tissue fluids will bridge a path for stray current being able to travel to surrounding tissue. As best seen in FIGS. 3A, 3B, 4 and 5, the electrode 310 may also include a pinch trim 331 that facilitates secure, integral engagement of the electrically insulating layer 211 (and 221) and jaw overmolding 314 (and 324) and the electrically conductive sealing surface 312 during the assembly and/or manufacturing process.

FIG. 6 shows a bipolar forceps 10 having an end effector assembly 1000 during use wherein handle members 16 and 18 are moved closer to one another to apply clamping force to the tubular tissue 150 to effect a seal 152. The end effector assembly 1000 may include first and second electrode jaw members 310 and 320, as previously described. Movement of the handle members 16 and 18 closer to one another is restricted by a gap set "G", which is established between the upper electrically conductive seal plate 312 and the lower electrically conductive seal plate 322 by the application of the electrically insulating seal layers 211 and 221, respectively. Once sealed, the tubular vessel 150 can be cut along seal 152 to separate the tissue 150 and form a gap in the tissue 150 therebetween.

It is envisioned that by making the electrode assembly 21 disposable, the electrode assembly 21 is less likely to become damaged since it is only intended for a single operation and, therefore, does not require cleaning or sterilization. As a result, the functionality and consistency of the sealing components, e.g., the electrically conductive surface 312 (and 322) and electrically insulating layer 211 (and 221) and jaw overmolding 314 (and 324) will assure a uniform and quality seal and provide a tolerable and reliable reduction of thermal spread across tissue. Alternatively, the entire electrosurgical instrument may be disposable, which, again, will assure a uniform and quality seal with minimal thermal spread.

Figure 7:
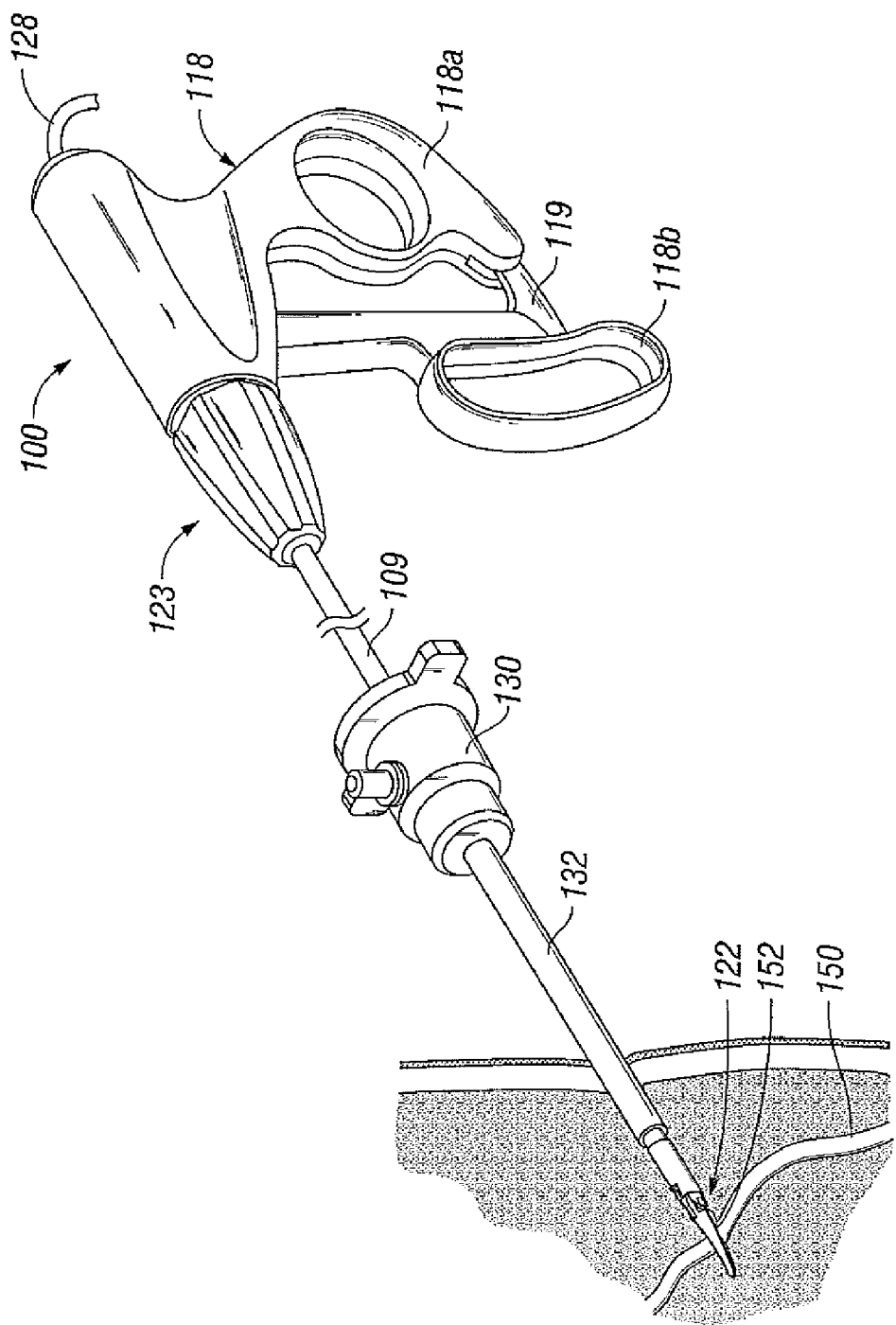
FIG. 7 is a perspective view of an endoscopic version of the present disclosure showing the operative motion of the instrument to effect sealing of a tubular vessel.

FIG. 7 shows an endoscopic bipolar instrument 100 during use wherein movement of a handle assembly 128 applies clamping force on the tubular tissue 150 to effect a seal 152. As shown, a shaft 109 and an end effector assembly or electrode assembly 122 are inserted through a trocar 130 and cannula 132 and a handle assembly 118 is actuated to cause opposing jaw members of the electrode assembly 122 to grasp tubular vessel 150 therebetween. More particularly, a movable handle 118b is moved progressively towards a fixed handle 118a, which, in turn, causes relative movement of the jaw members from an open, spaced-apart position to a closed, sealing position. A rotating member 123 allows the user to rotate the electrode assembly 122 into position about the tubular tissue 150 prior to activation. End effector assembly 122 may include first and second electrode jaw members 310 and 320, respectively, as described previously.

After the jaw members 310 and 320 are closed about the tissue 150, the user then applies electrosurgical energy via connection 128 to the tissue 150. By controlling the intensity, frequency and duration of the electrosurgical energy applied to the tissue 150, the user can either cauterize, coagulate/desiccate seal and/or simply reduce or slow bleeding with minimal collateral or thermal damage to surrounding tissue.

An electrosurgical forceps such as, for example but not limited to, open bipolar instrument 10 and end effector assembly 1000 (see FIG. 6) and endoscopic bipolar instrument 100 and electrode assembly 122 (see FIG. 7), may include a knife channel for passage of a knife for cutting tissue during surgical procedures.

From the foregoing and with reference to the various figure drawings, those skilled in the art will appreciate that certain modifications can also be made to the present disclosure without departing from the scope of the present disclosure.

For example, although it is preferable that electrodes 310 and 320 meet in parallel opposition and, therefore, meet on the same plane, in some cases it may be preferable to slightly bias the electrodes 310 and 320 to meet each other at a distal end such that additional closure force on the handles 16 and 18 is required to deflect the electrodes in the same plane. It is envisioned that this could improve seal quality and/or consistency.

Although it is preferable that the electrode assembly 21 include housing 71 and cover plate 80 to engage mechanical forceps 20 therebetween, in some cases it may be preferable to manufacture the electrode assembly 21 such that only one piece, e.g., housing 71 is required to engage mechanical forceps 20.

The outer surface of the end effectors may include a nickel-based material, coating, stamping, metal injection molding that is designed to reduce adhesion between the end effectors (or components thereof) with the surrounding tissue during or after sealing.

One embodiment of the foregoing method for manufacturing the jaw member 310 or 320 of an end effector assembly 1000 or 122 for use with an electrosurgical instrument 10 or 100, respectively, includes the steps of providing an electrically conductive tissue engaging plate 312 or 322 and a jaw support 319 or 329 (See FIGS. 2A and 3A); covering one side 312' or 322' of the electrically conductive tissue engaging plate 312 or 322 with an electrically insulative, thermally non-degrading coating 211 or 221; placing and securing the electrically conductive tissue engaging plate 312 or 322 and the jaw support 319 or 329 into a jaw mold (not shown) and introducing a liquid substance (not shown) into the jaw mold and allowing the liquid substance (not shown) to cure around the electrically conductive tissue engaging plate 312 or 322 and the jaw support 319 or 329. The liquid substance may be selected from the group consisting of liquid crystal polymer, thermoplastic polymer, epoxy and silicone. The coating 211 or 221 of the covering step may be of uniform thickness across the electrically conductive tissue engaging plate 312 or 322. In addition, the coating 211 or 221 of the covering step may include a thickness that provides the gap-set "G" between the electrically conductive tissue engaging plate 312 or 322 and the jaw support 319 or 329 during the introducing step (see FIG. 6).

In another particularly useful embodiment, as best illustrated in FIGS. 2A and 3A, the insulating layer 211 and 221 of electrode 310 and 320 is attached to opposite side seal surface 312' and 322' via application of adhesive 251. As discussed previously, the adhesive 251 may include a material that includes polyurethane or other materials. Again, in this case, the application of the jaw over molding 314 and 324 over the insulating layer 211 and 221, respectively, is optional. Those skilled in the art will recognize that adhesive 251 may be applied in a similar manner to the insulating layer 221 of electrode 320 and seal surface 322.

Again, by applying a coating of electrically insulating layer 211 and 221 onto one side 312' and 322' of electrically conductive seal plates 312 and 322, respectively, enhanced thermal and electrical properties are provided so as to increase electrical and thermal isolation during activation and may be dimensioned to regulate the gap distance "G" to within a preferred gap range as described in more detail previously with respect to FIG. 6.

More particularly, referring to FIG. 6, one embodiment relating to the foregoing method for manufacturing the jaw member 110 or 120 of the end effector assembly 1000 for use with the electrosurgical instrument 10 or 100. The method includes the steps of: providing the electrically conductive tissue engaging plate 312 or 322 and the jaw support 319 or 329; covering one side 312' or 322' of the electrically conductive tissue engaging plate 312 or 322 with the electrically insulative, thermally non-degrading coating 211 or 221; and securing the side 312' or 322' of the electrically conductive tissue engaging plate 312 or 322 onto the jaw support 319 or 329 with the adhesive 251. The coating 211 or 221 of the covering step may be of uniform thickness across the electrically conductive tissue engaging plate 312 or 322. The coating 211 or 221 of the covering step may include a thickness that provides the gap-set "G" between the electrically conductive tissue engaging plate 312 or 322 and the jaw support 319 or 329 during the introducing step (see FIG. 6).

While more than one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A method for manufacturing a jaw member of an end effector assembly for use with an electrosurgical instrument, the method comprising the steps of:
   providing an electrically conductive tissue engaging plate, said electrically conductive tissue engaging plate having vertically-extending edges extending about a periphery and along a length thereof of said electrically conductive plate, and a jaw support;
   covering one side of the electrically conductive tissue engaging plate and said vertically-extending edges with an electrically insulative, thermally non-degrading coating; and
   securing the electrically insulative, thermally non-degrading coating covering the one side and said vertically-extending edges of the electrically conductive tissue engaging plate onto the jaw support with an adhesive.

2. A method according to claim 1 wherein the step of covering includes covering the one side of the electrically conductive tissue engaging plate and said vertically-extending edges with an electrically insulative, thermally non-degrading coating with one of flame sprayed ceramic, vapor deposition polymer, an oxide layer, and an anodized coating.

3. A method according to claim 1 wherein the step of securing includes securing the electrically insulative, thermally non-degrading coating covering the one side and said vertically-extending edges of the electrically conductive tissue engaging plate onto the jaw support with an adhesive that includes polyurethane.

4. A method according to claim 1 wherein the step of covering includes covering one side of the electrically conductive tissue engaging plate and said vertically-extending edges with an electrically insulative, thermally non-degrading coating of uniform thickness across the electrically conductive tissue engaging plate.

5. A method according to claim 1 wherein the step of covering includes covering one side of the electrically conductive tissue engaging plate and said vertically-extending edges with an electrically insulative, thermally non-degrading coating that includes a thickness that provides a gap-set between the electrically conductive tissue engaging plate and the jaw support during the securing step.

* * * * *